(12) United States Patent
Benhabbour et al.

(10) Patent No.: US 12,409,134 B2
(45) Date of Patent: Sep. 9, 2025

(54) GEOMETRICALLY COMPLEX INTRAVAGINAL RINGS, SYSTEMS AND METHODS OF MAKING THE SAME

(71) Applicant: The University of North Carolina at Chapel Hill, Chapel Hill, NC (US)

(72) Inventors: Soumya Rahima Benhabbour, Chapel Hill, NC (US); Rima Januszewicz, Durham, NC (US); Sue J. Mecham, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 773 days.

(21) Appl. No.: 17/572,196

(22) Filed: Jan. 10, 2022

(65) Prior Publication Data

US 2022/0168218 A1 Jun. 2, 2022

Related U.S. Application Data

(60) Division of application No. 16/139,481, filed on Sep. 24, 2018, now Pat. No. 11,219,595, which is a
(Continued)

(51) Int. Cl.
*A61K 9/00* (2006.01)
*A61F 6/08* (2006.01)
(Continued)

(52) U.S. Cl.
CPC ............. *A61K 9/0036* (2013.01); *A61F 6/08* (2013.01); *A61K 31/565* (2013.01); *A61K 31/57* (2013.01);
(Continued)

(58) Field of Classification Search
CPC .................................................. A61K 9/0036
See application file for complete search history.

(56) References Cited

U.S. PATENT DOCUMENTS 4,822,616 A 4/1989 Zimmermann et al.
5,156,623 A 10/1992 Hakamatsuka et al.
(Continued)

FOREIGN PATENT DOCUMENTS

EP 4129300 A1 2/2023
WO 2014126837 A2 8/2014
(Continued)

OTHER PUBLICATIONS

Huttunen, Jani. "Effectiveness of 3D Printing in Small Scale Production." (2015). (Year: 2015).*
(Continued)

*Primary Examiner* — Susan D Leong
*Assistant Examiner* — Vipul Malik
(74) *Attorney, Agent, or Firm* — KDW FIRM PLLC

(57) ABSTRACT

Geometrically complex intravaginal rings, systems and methods of making the same are provided herein. Disclosed herein are geometrically complex intravaginal rings with tunable and enhanced drug release, which in some embodiments can be fabricated by 3D printing technologies. The disclosed IVRs include a ring structure comprising a plurality of unit cells or macroscopic and/or microscopic architecture, which can be tuned to control the loading capacity of an active compound within the IVR, the diffusion of an active compound from the IVR, the surface area of the IVR, and/or the mechanical properties of the IVR. The disclosed geometrically complex IVRs can provide superior control over drug loading and drug release compared to conventional IVRs fabricated by injection molding or hot-melt extrusion.

18 Claims, 17 Drawing Sheets

Related U.S. Application Data continuation of application No. PCT/US2017/023777, filed on Mar. 23, 2017.

(60) Provisional application No. 62/312,268, filed on Mar. 23, 2016.

(51) Int. Cl.

| | | |
|---|---|---|
| *A61K 31/565* | (2006.01) | |
| *A61K 31/57* | (2006.01) | |
| *A61K 31/675* | (2006.01) | |
| *A61M 31/00* | (2006.01) | |
| *B29C 64/00* | (2017.01) | |
| *B29C 64/124* | (2017.01) | |
| *B29C 64/135* | (2017.01) | |
| *B29L 31/00* | (2006.01) | |
| *B33Y 10/00* | (2015.01) | |
| *B33Y 30/00* | (2015.01) | |
| *B33Y 70/00* | (2020.01) | |
| *B33Y 80/00* | (2015.01) | |
| *A61K 31/566* | (2006.01) | |
| *B29K 105/00* | (2006.01) | |
| *B29K 283/00* | (2006.01) | |

(52) U.S. Cl.
CPC ........... *A61K 31/675* (2013.01); *A61M 31/00* (2013.01); *A61M 31/002* (2013.01); *B29C 64/00* (2017.08); *B29C 64/124* (2017.08); *B33Y 30/00* (2014.12); *B33Y 70/00* (2014.12); *B33Y 80/00* (2014.12); *A61K 31/566* (2013.01); *A61M 2207/00* (2013.01); *B29C 64/135* (2017.08); *B29K 2105/0035* (2013.01); *B29K 2283/00* (2013.01); *B29K 2995/0093* (2013.01); *B29L 2031/753* (2013.01); *B33Y 10/00* (2014.12)

(56) References Cited

U.S. PATENT DOCUMENTS

| | | |
|---|---|---|
| 2003/0049302 A1 | 3/2003 | Pauletti et al. |
| 2004/0023867 A1 | 2/2004 | Daniels et al. |
| 2007/0043332 A1* | 2/2007 | Malcolm .............. A61K 9/0036 604/500 |
| 2009/0004246 A1* | 1/2009 | Woolfson ........... C07K 16/1063 424/430 |
| 2010/0040671 A1 | 2/2010 | Ahmed et al. |
| 2014/0128345 A1 | 5/2014 | Woodrow et al. |
| 2014/0328884 A1 | 11/2014 | Reyes et al. |
| 2016/0263837 A1* | 9/2016 | Goldman .............. B29C 64/386 |
| 2017/0120515 A1 | 5/2017 | Rolland et al. |
| 2018/0008536 A1* | 1/2018 | Jukarainen ............ B33Y 80/00 |
| 2019/0091141 A1 | 3/2019 | Benhabbour et al. |

FOREIGN PATENT DOCUMENTS

| | | | |
|---|---|---|---|
| WO | 2015013716 A1 | 1/2015 | |
| WO | 2016016502 A1 | 2/2016 | |
| WO | WO-2017077520 A1 * | 5/2017 | ............ A61K 47/34 |
| WO | 2017165624 A1 | 9/2017 | |

OTHER PUBLICATIONS

Chen, Yufei. "Development and evaluation of novel intravaginal rings fabricated via hot-melt extrusion-based technologies as innovative microbicides." (2014). (Year: 2014).*

European Search Report for Application No. 22189453 mailed Jan. 5, 2023.

Canadian Office Action for Application No. 3018148 mailed Jan. 7, 2023.

Office Action corresponding to U.S. Appl. No. 16/139,481, dated Apr. 12, 2021.

Notice of Allowance corresponding to U.S. Appl. No. 16/139,481, dated Aug. 19, 2021.

European Office Action in EP Application No. 22189453.8, dated Nov. 28, 2024, 7 pages.

* cited by examiner

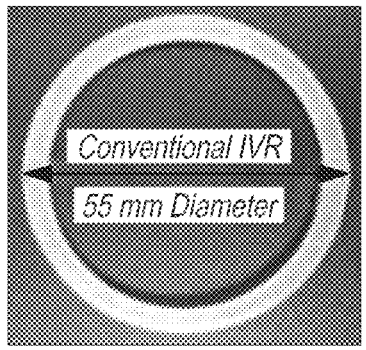 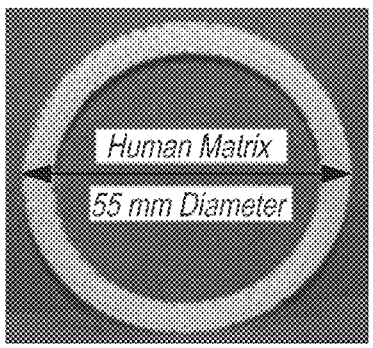 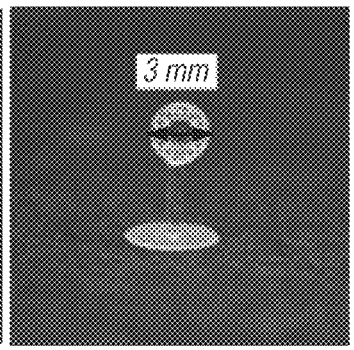
FIG. 2A　　　　　FIG. 2B　　　　　FIG. 2C
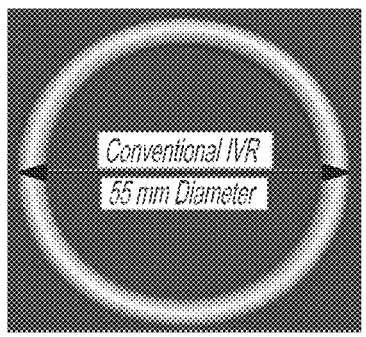 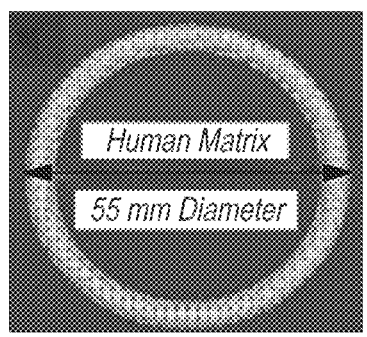 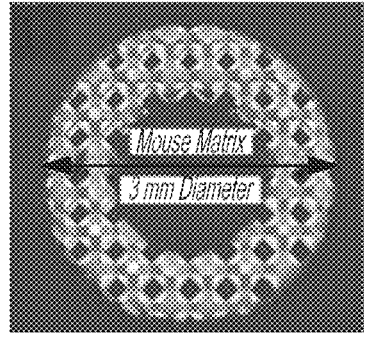
FIG. 2D　　　　　FIG. 2E　　　　　FIG. 2F

| Design | | Unit Cell | Design | OD (mm) | CS (mm) | #UC/CS | SA (mm$^2$) | Volume (mm$^3$) | SSA (1/m) | Volume Fraction |
|---|---|---|---|---|---|---|---|---|---|---|
| A |  |  | B banded | 54 | 7.6 | 2 | 14,599 | 2,110 | 6.9 | 0.32 |
| B | | | B banded | 54 | 7.6 | 3 | 19,467 | 2,106 | 9.2 | 0.32 |
| C | | | B banded | 54 | 7.6 | 4 | 24,339 | 2,108 | 11.5 | 0.32 |
| D | | | B banded | 54 | 7.6 | Trimodal | 20,145 | 3,009 | 6.7 | 0.46 |
| E | |  | D banded | 54 | 7.6 | 2.925 | 17903 | 1897 | 9.4 | 0.29 |
| F | |  | E banded | 54 | 7.6 | 2.925 | 14463 | 1107 | 13.1 | 0.17 |
| G | | | B | 54 | 4 | 2 | 6100 | 548 | 11.1 | 0.28 |
| H | | | B banded | 54 | 4 | 2 | 7516 | 630 | 11.9 | 0.32 |
| I | | | B banded | 54 | 4 | 3 | 10275 | 628 | 16.4 | 0.32 |
| J | | | B banded | 54 | 4 | 4 | 13014 | 628 | 20.7 | 0.32 |
FIG. 6

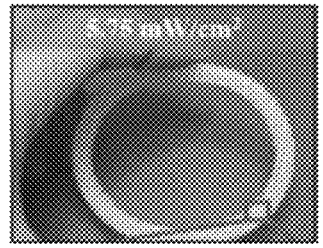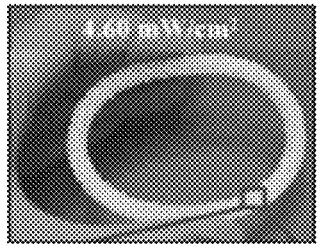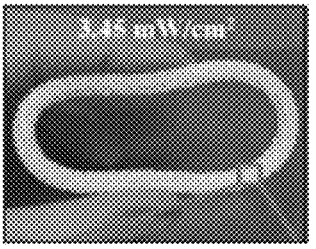
FIG. 7A    FIG. 7C    FIG. 7E
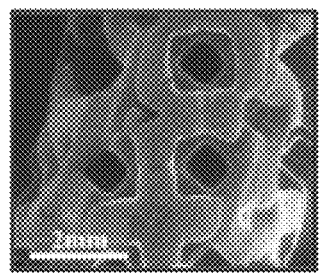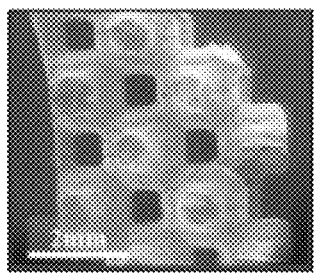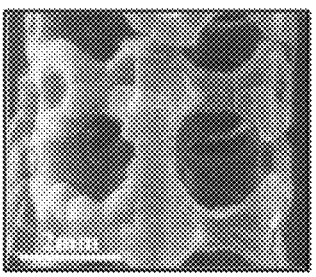
FIG. 7B    FIG. 7D    FIG. 7F
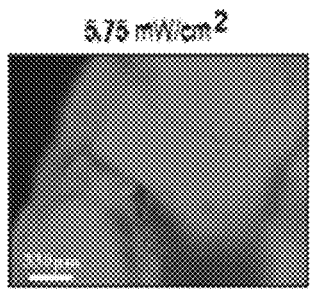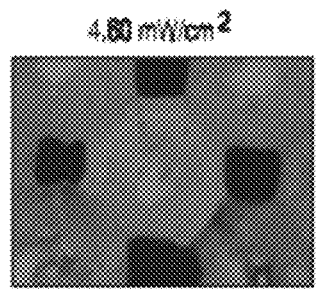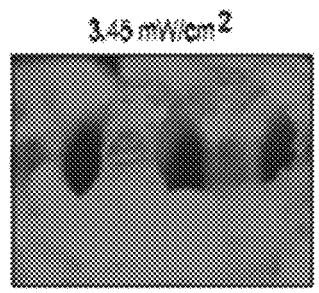
FIG. 8A    FIG. 8C    FIG. 8E
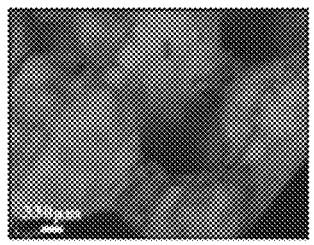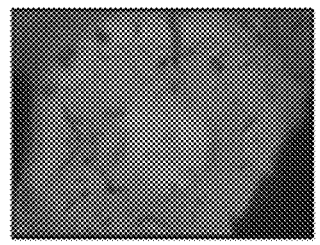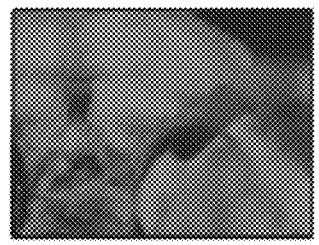
FIG. 8B    FIG. 8D    FIG. 8F

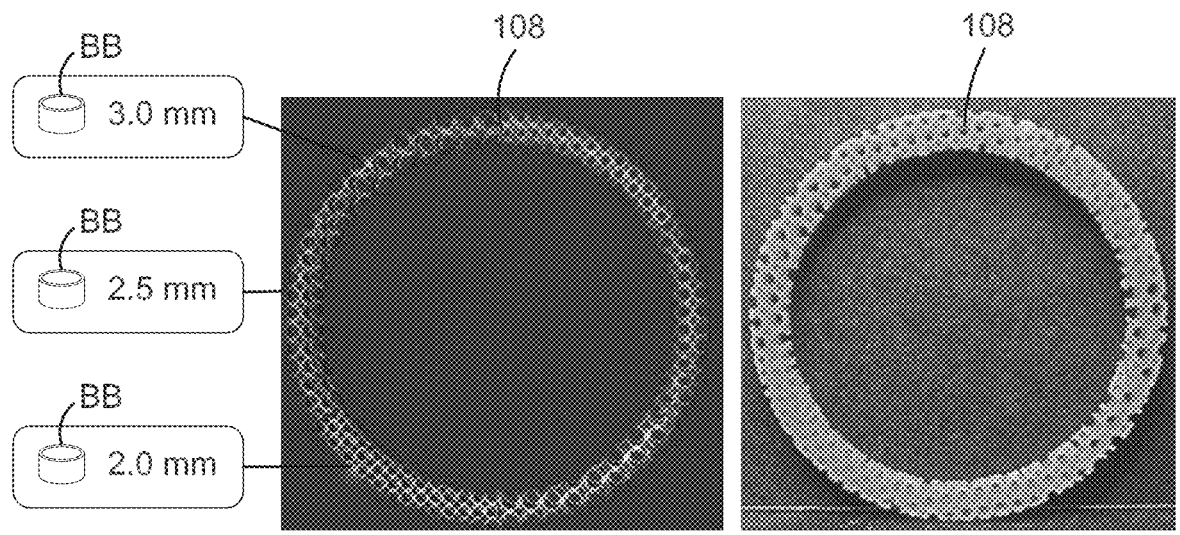
FIG. 11A  FIG. 11B
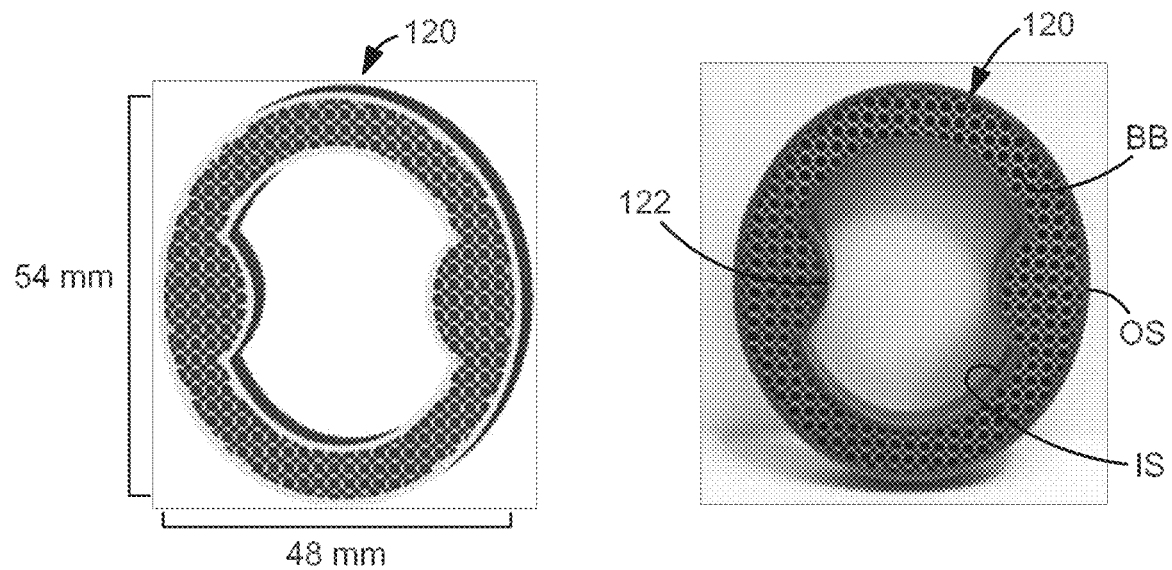
FIG. 12A  FIG. 12B

GEOMETRICALLY COMPLEX INTRAVAGINAL RINGS, SYSTEMS AND METHODS OF MAKING THE SAME

CROSS-REFERENCE TO RELATED APPLICATIONS

This application is a divisional of U.S. patent application Ser. No. 16/139,481 filed Sep. 24, 2018, which is a continuation of International Patent Application Serial No. PCT/US2017/023777, filed Mar. 23, 2017, which claims the benefit of U.S. Provisional Patent Application Ser. No. 62/312,268, filed Mar. 23, 2016, the disclosures of which are incorporated herein by reference in their entireties.

TECHNICAL FIELD

Disclosed herein are geometrically complex intravaginal rings, systems and methods of making the same. Geometrically complex intravaginal rings with tunable and enhanced drug release, which in some embodiments can be fabricated by 3D printing technologies, are also disclosed.

BACKGROUND

Despite decades of research an estimated 36.9 million people were living with HIV and about 2.0 million people were newly infected with the virus in 2014 globally [1]. Thus, it is imperative that effective HIV prevention tools are developed and rapidly implemented. Oral pre-exposure prophylaxis (PrEP) with the daily pill TRUVADA® is an effective prevention intervention for HIV acquisition, particularly when adherence is high [2-5]. However, oral PrEP trials utilizing daily dosing of antiretrovirals (ARVs) have yielded disparate efficacy results (0-83%), attributed to unpredictable tissue drug penetration and variable adherence [6]. Additionally, HIV and other sexually transmitted infections occur via the female genital tract (FGT); however, conventional treatment and prevention strategies involve oral administration of drugs. Most of these therapeutic strategies have failed as a result of high liver metabolism of orally administered drugs before being absorbed into the systemic circulation and reaching the FGT. Increasing the administered dose is not always a viable option due to severe systemic toxicity. Therefore, local drug delivery via the vagina could in some cases be the ideal strategy for treatment of infections or disease affecting the FGT.

Innovations recently introduced into the field of systemic PrEP are long acting (LA) formulations of ARVs that stably release drugs over many weeks [7, 8]. Intravaginal rings represent a sustained-release approach to microbicide delivery and are one strategy to improve adherence and drug delivery. This is particularly important considering the fact that more than 50% of those infected with HIV are women with heterosexual transmission as the main route of infection [9].

The field of HIV PrEP is in desperate need for new technologies that utilize efficient and cost effective engineering to manufacture devices with high patient adherence and long acting delivery of antiretroviral drugs. Current technologies utilize either traditional injection molding or hot-melt extrusion to manufacture intravaginal rings (IVRs). An inherent drawback with these processes is the effect of the high temperatures and pressures on drug or biologic's stability and dispersion within the resin during fabrication. These technologies are limiting in many ways including a) the choice of starting materials (i.e. Polydimethylsiloxane (PDMS), ethylene-vinyl acetate (EVA), or polyurethane (PU)), b) minimal and restricted complexity of design, c) limited range of drug diffusion rate due to simple IVR design (e.g. conventional matrix IVR), and d) complex stepwise processes to produce multi-purpose IVRs.

The field of HIV PrEP also needs new devices that can 1) release drugs over longer periods of time (>30 days), 2) enhance efficacy in preventing against HIV transmission, and 3) can integrate two or more drugs to prevent HIV and other STDs as well as unwanted pregnancies. The development of multipurpose prevention could be ground breaking, as there are no approved products that use two drugs to simultaneously address multiple indications (e.g. HIV and unwanted pregnancies) and potential drug resistance. Developing effective multipurpose IVRs has proven to be challenging due to differences in drug properties and target release rates, mandating the investigation of customized IVR designs. Therefore, there is an unmet need for IVR technologies that have the potential to provide precise and tunable control over the drug release rates for as long as several months.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, provided herein are geometrically complex intravaginal rings (IVRs). The IVRs can comprise a three dimensional ring structure comprising a body forming an inner diameter and an outer diameter, a plurality of unit cells, the unit cells comprising a macroscopic and/or microscopic architecture, wherein the plurality of unit cells together form the body of the ring structure, and an active compound, wherein the macroscopic architecture and/or microscopic architecture of the unit cells is configured to control a loading capacity of the active compound within or on the IVR, a diffusion rate of the active compound from the IVR, a surface area of the IVR, a fractional volume of the IVR, and/or a mechanical property of the IVR.

Also provided herein are methods of fabricating IVRs, including 3D printing methodologies. Such methods can in some aspects comprise providing a template for an IVR, the template comprising a three dimensional ring structure comprising a plurality of unit cells, macroscopic architecture and/or microscopic architecture, providing a material from which the IVR is to be fabricated, providing a 3D printing system, and producing an IVR from the material using the 3D printing device based on the template.

In some embodiments provided herein are methods of treating a subject using an IVR disclosed herein. Such methods of treatment can comprise providing a subject in need of treatment, providing a geometrically complex IVR with an active agent therein, and placing the IVR intravaginally in the subject, whereby the subject is treated. In some aspects the IVR can be designed such that the macroscopic architecture and/or microscopic architecture of the unit cells is configured to control a loading capacity of the active compound within the IVR, a diffusion rate of the active compound from the IVR, a surface area of the IVR, and/or a mechanical property of the IVR.

The foregoing and other objects and aspects of the present disclosure are explained in detail in the specification set forth below.

Embodiments of the presently disclosed subject matter having been stated hereinabove, and which is achieved in whole or in part by the presently disclosed subject matter, other embodiments will become evident as the description proceeds when taken in combination with the accompanying Examples as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings.

FIGS. 2A through 2F are images of human size IVR and a mouse size IVR. FIG. 2A is a photograph of a conventional human size solid matrix IVR (55 mm outer diameter (O.D.), 5 mm cross sectional diameter (C.S.)) fabricated by injection molding. FIG. 2B is a photograph of a human size IVR with complex inner geometry fabricated with CLIP (55 mm O.D., 5 mm C.S.). FIG. 2C is a mouse size IVR with complex inner geometry fabricated with CLIP (3 mm O.D., 1 mm C.S.). Corresponding IVR CAD files are illustrated in FIGS. 2D through 2F.

FIGS. 3A, 3C and 3E are photographs of fabricated IVRs, with corresponding ESEM images in FIGS. 3B, 3D and 3F, respectively.

FIG. 4A illustrates unit cell types AA, BB and CC, geometrically complex IVRs made from those exemplary cell types, and the resulting surface area of each. FIG. 4B illustrates unit cell types DD and EE.

FIG. 6 is a table summarizing exemplary CAD IVR designs, including illustrations, and nomenclatures used in the in vitro studies described herein.

FIGS. 7A through 7F are ESEM images of prototype IVRs fabricated using the same resin and design with varying light intensity (photon flux) using the CLIP process, which shows the effect of photon flux on inner geometry and mechanical properties. FIGS. 7A, 7C and 7E are photographs of the IVRs, and FIGS. 7B, 7D and 7F are corresponding ESEM images. FIG. 7A shows an IVR fabricated at high light intensity (5.75 mW/cm$^2$), with a close-up view shown in FIG. 7B. FIG. 7C shows an IVR fabricated at medium light intensity (4.60 mW/cm$^2$), with a close-up view shown in FIG. 7D. FIG. 7E shows an IVR fabricated at low light intensity (3.45 mW/cm$^2$), with a close-up view shown in FIG. 7F.

Fluorescence imaging is shown in FIGS. 8A through 8F. Cross-sectional views are shown at two magnifications for prototype IVRs fabricated at varying light intensities of 5.75 mW/cm$^2$ (FIGS. 8A and 8B), 4.60 mW/cm$^2$, and (FIGS. 8C and 8D), and 3.45 mW/cm$^2$ (FIGS. 8E and 8F). Distribution of fluorophore (0.01 wt. % rhodamine-B) appears homogenous throughout the cross-section of each IVR fabricated with the CLIP process.

Figure 9A:
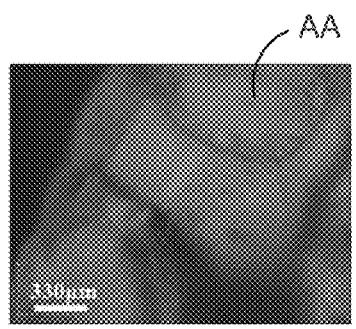
Figure 9C:
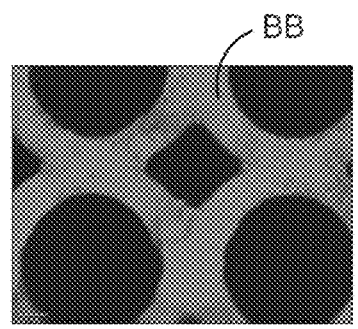
Figure 9E:
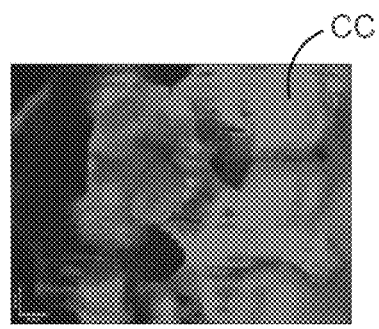
Figure 9B:
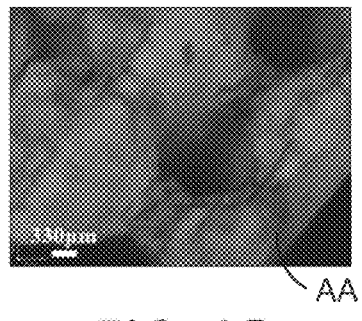
Figure 9D:
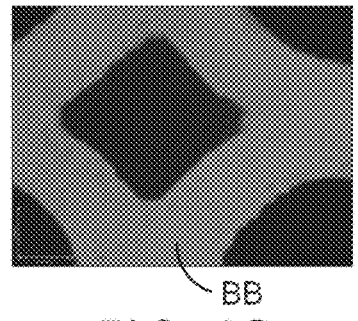
Figure 9F:
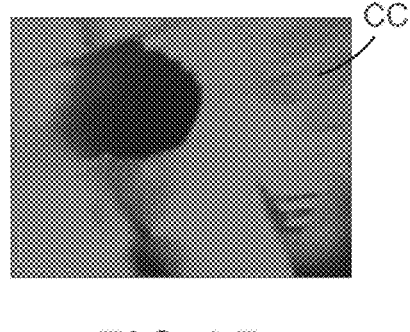

FIGS. 9A through 9F are fluorescence images of cross-sectional views, at two magnifications, of each of unit cells AA (FIGS. 9A and 9B) BB (FIGS. 9C and 9D) and CC (FIGS. 9E and 9F).

Figure 10A:
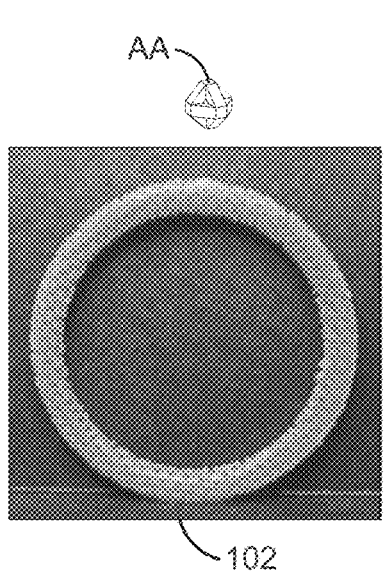
Figure 10B:
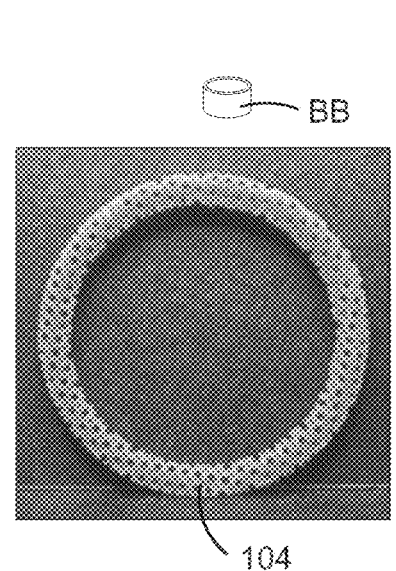
Figure 10C:
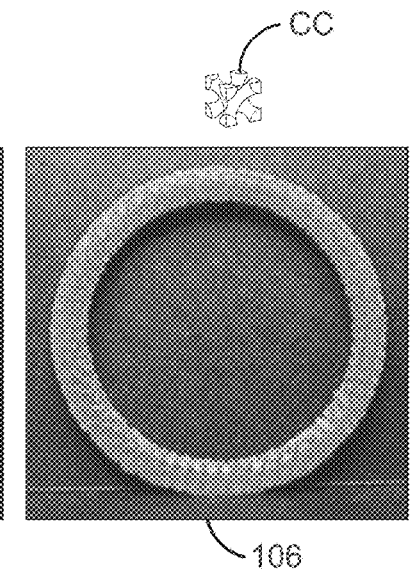

FIGS. 10A through 10C are images of IVRs fabricated with three different unit cells (unit cells AA in IVR 102, FIG. 10A; unit cells BB in IVR 104, FIG. 10B, and unit cells CC in IVR 106, FIG. 10C).

FIGS. 11A and 11B show intravaginal rings containing three unit cells of varying size (3.0 mm, 2.5 mm and 2.0 mm) fabricated using CLIP with a PEG 700 diacrylate resin. FIG. 11A is an image of a CAD file design of multi unit cell IVR, while FIG. 11B is an image of a CLIP human size IVR containing 0.01% w/w rhodamine-B (55 mm O.D., 5 mm C.S.).

FIGS. 12A and 12B are images of unsymmetrical IVRs. FIG. 12A is an illustration of a CAD file of an example oval-shaped IVR. FIG. 12B is an image of a prototype 3D printed IVR.

Figure 13:
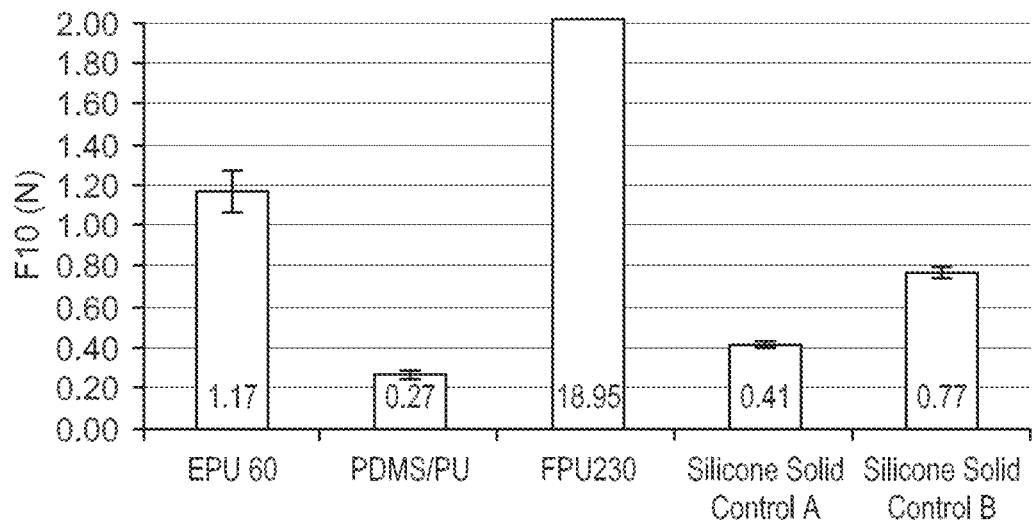

FIG. 13 is a bar graph showing mechanical property results of a comparison of 3D printed IVRs with the same complex design based on the BB unit cell arrayed three times across the 7.6 mm cross section including a band on both the inner and outer diameter of the IVR.

Figure 14:
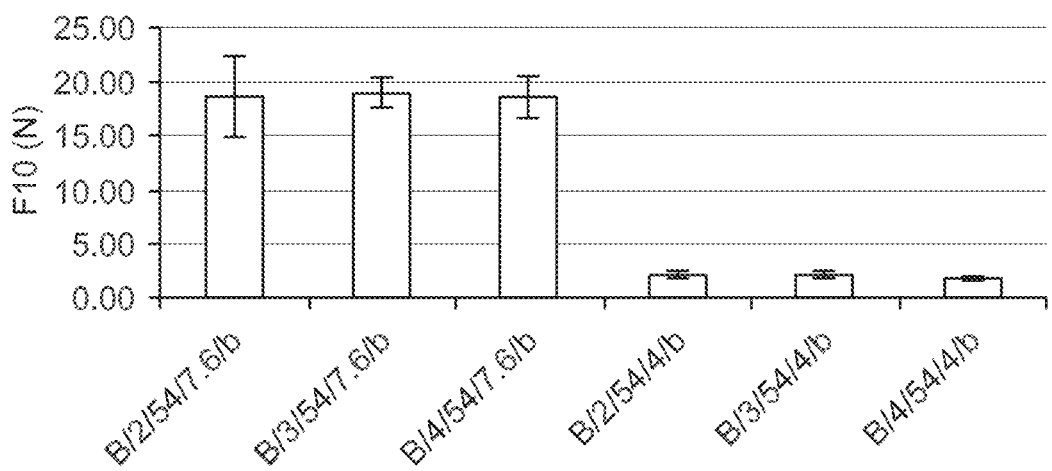

FIG. 14 is a bar graph showing mechanical property results of a comparison of IVRs made using the same resin and the same unit cell and same added design features with different numbers of unit cells arrayed and different cross sectional diameters.

Figure 15:
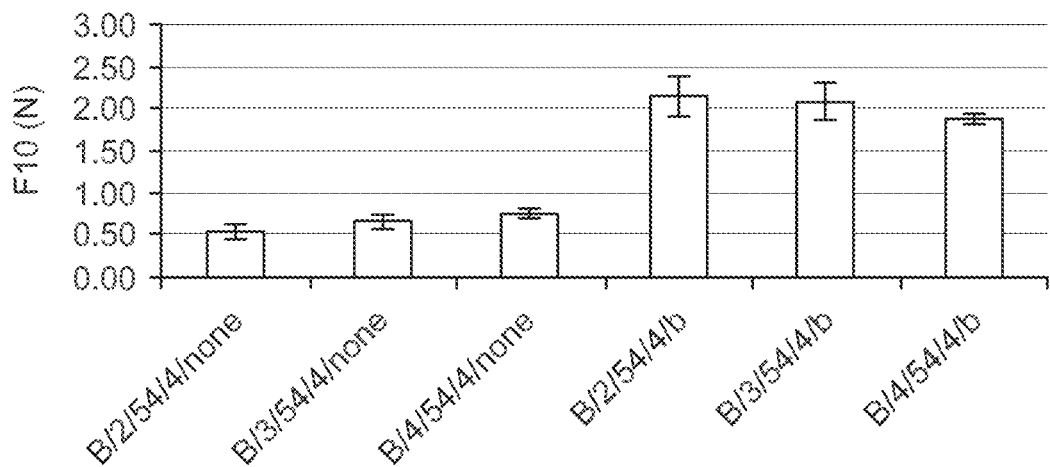

FIG. 15 is a bar graph showing mechanical property results of a comparison of IVRs made using the same resin and the same unit cell and arrays with and without the added design features of the banding on the inner and outer diameter.

Figure 16:
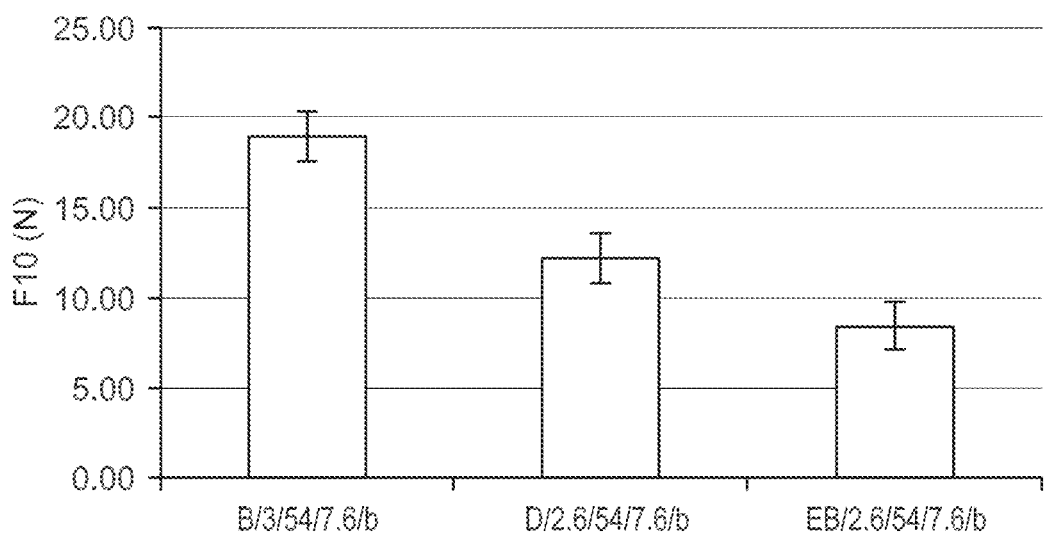

FIG. 16 is a bar graph showing mechanical property results of a comparison of IVRs of the same size and material and the same added design features with three different unit cell designs of the same size.

Figure 17:
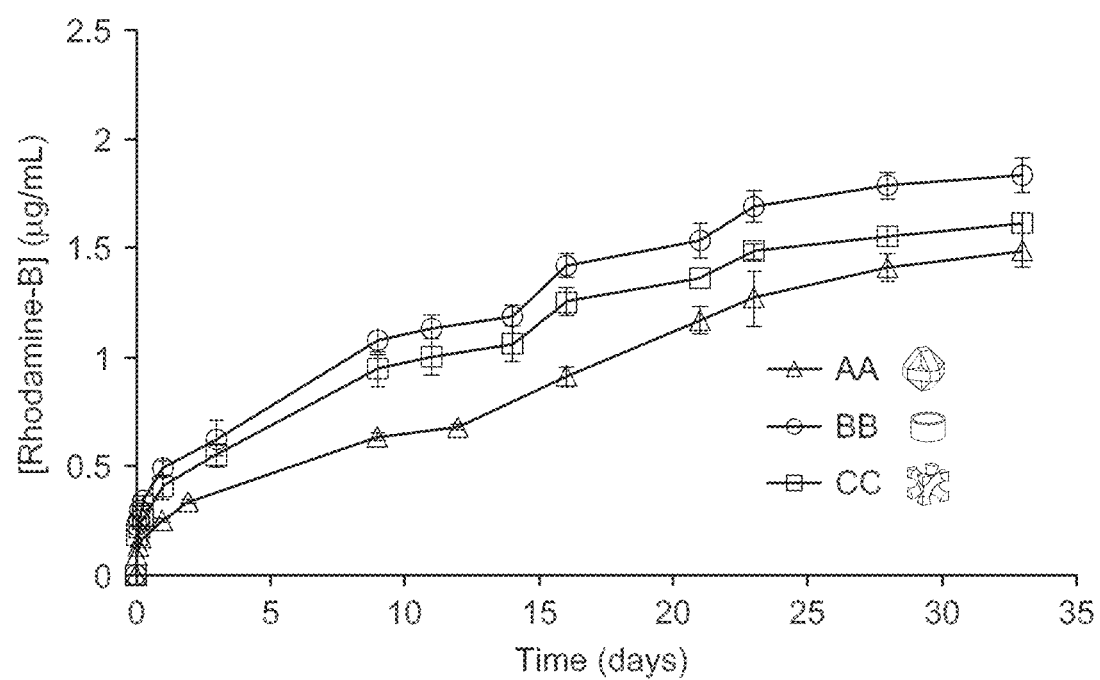

FIG. 17 is a scatter plot of the in vitro release of rhodamine-B from geometrically complex IVRs (N=3) over 33 days at 37° C. in a simulated vaginal fluid (SVF) (25 mM NaOAc buffer, pH 4.2) comparing IVRs with different unit cells, including AA IVR with 10114 mm$^2$ specific surface area, BB IVR with 7688 mm$^2$ specific surface area, and CC IVR with 7404 mm$^2$ specific surface area.

Figure 18:
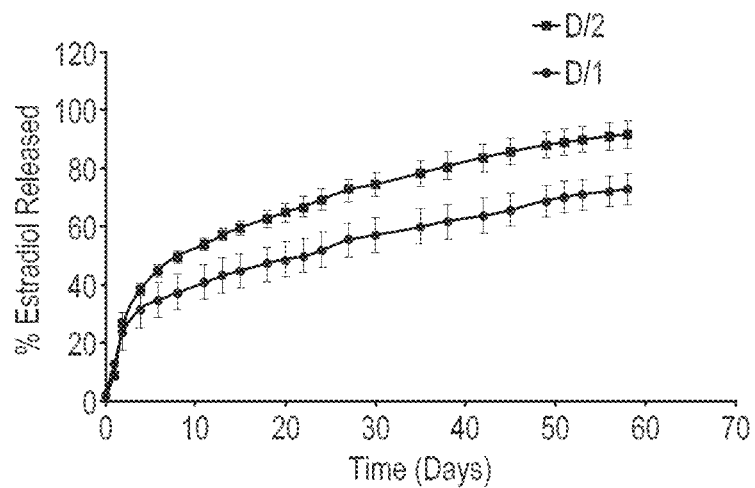

FIG. 18 is a graphical depiction of the results analyzing the effect of surface area on release kinetics of β-Estradiol.

Figure 19:
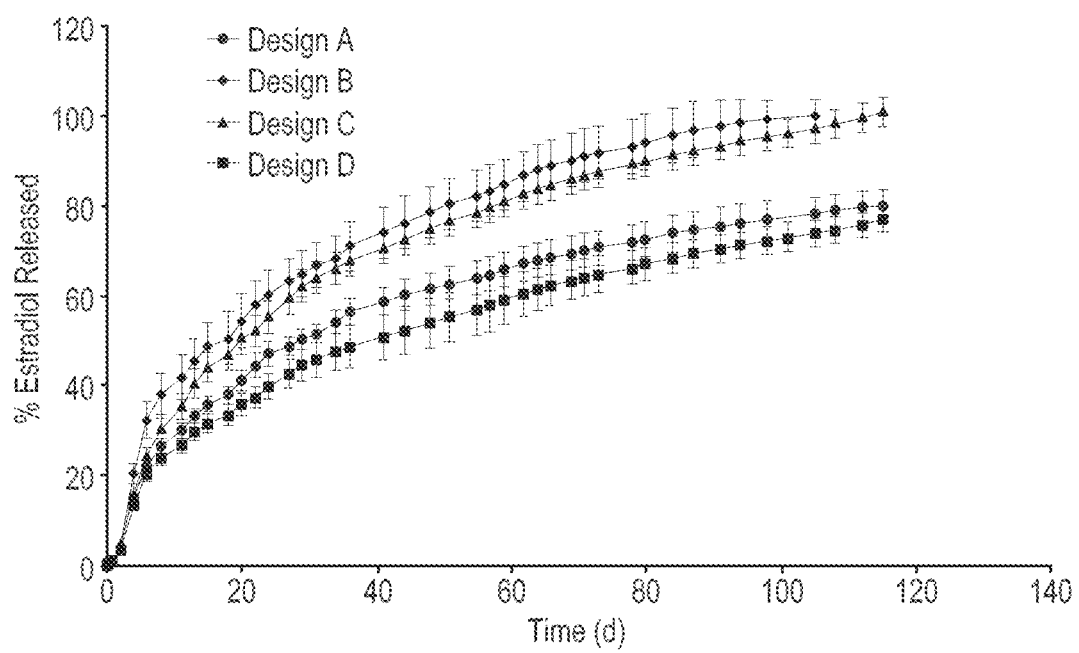

FIG. 19 is a graphical depiction of the results of in vitro release kinetics of β-Estradiol in B series IVRs.

Figure 20:
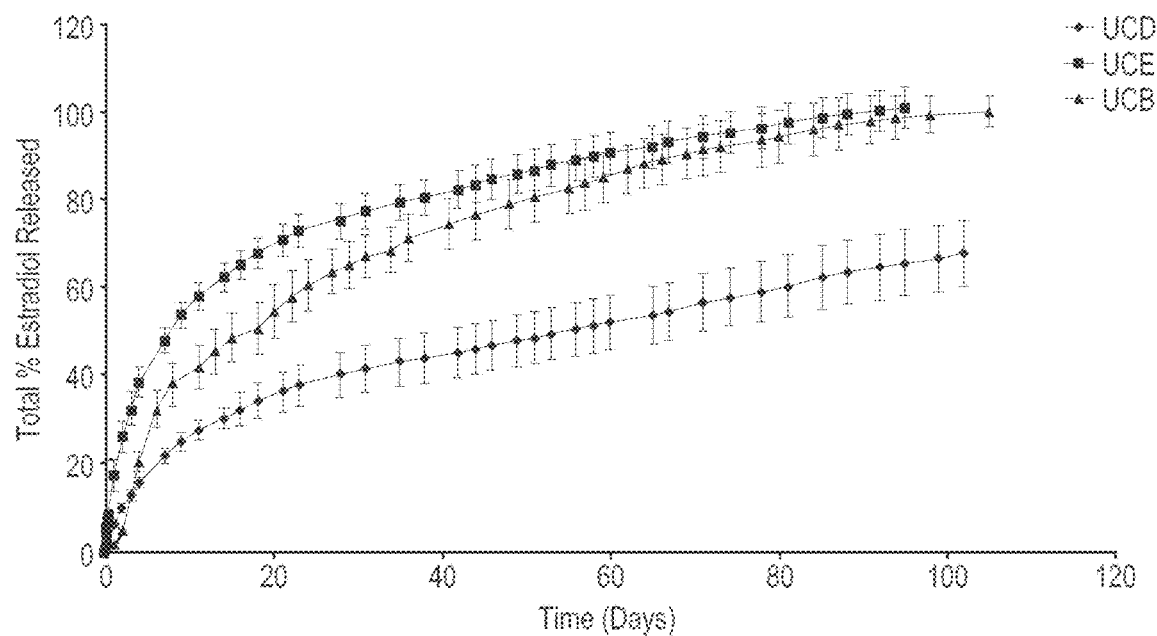

FIG. 20 is a graphical depiction of the results of in vitro release kinetics of β-Estradiol comparing B, D, and E series IVRs.

Figure 21:
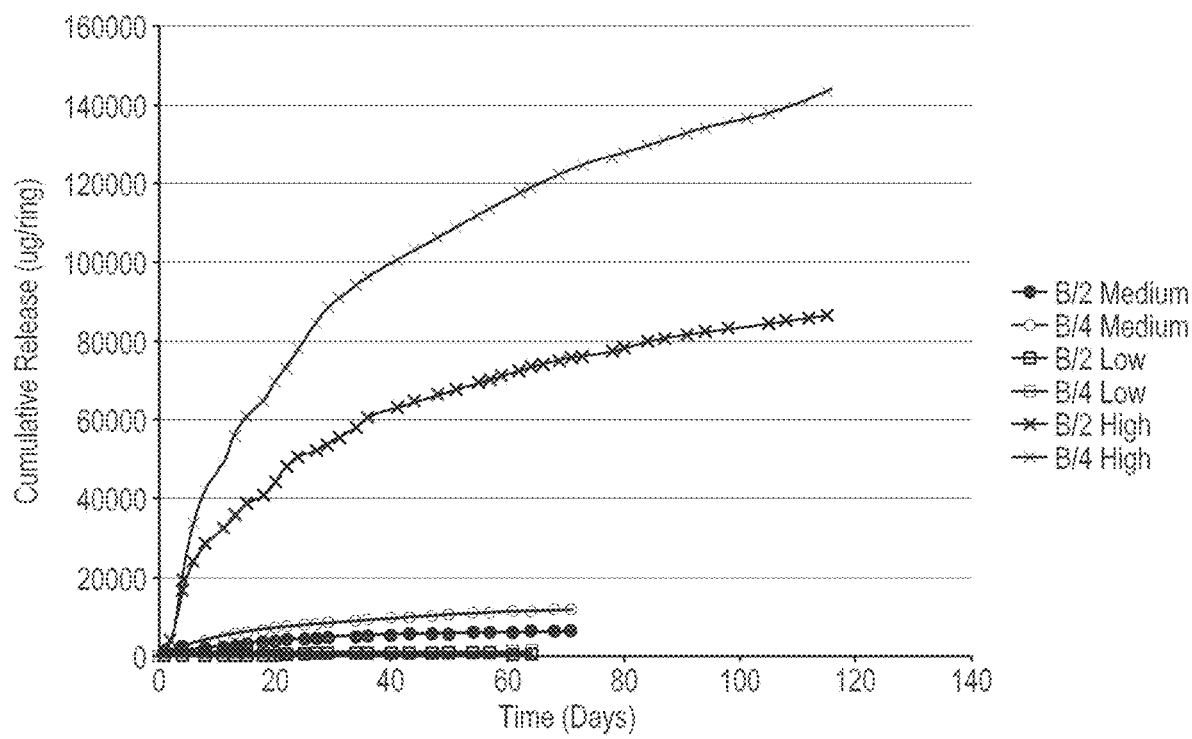
Figure 22:
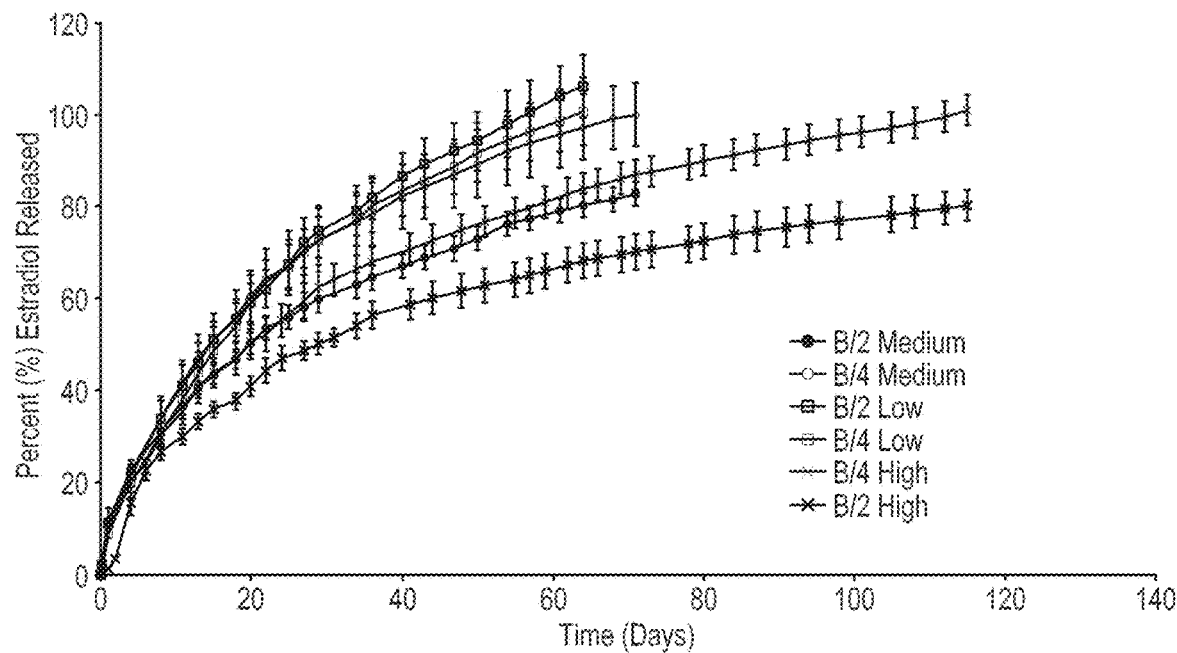

FIGS. 21 and 22 are graphical depictions of the results of in vitro release kinetics of β-Estradiol comparing B series IVRs, with FIG. 21 showing cumulative release and FIG. 22 showing percent release.

Figure 23A:
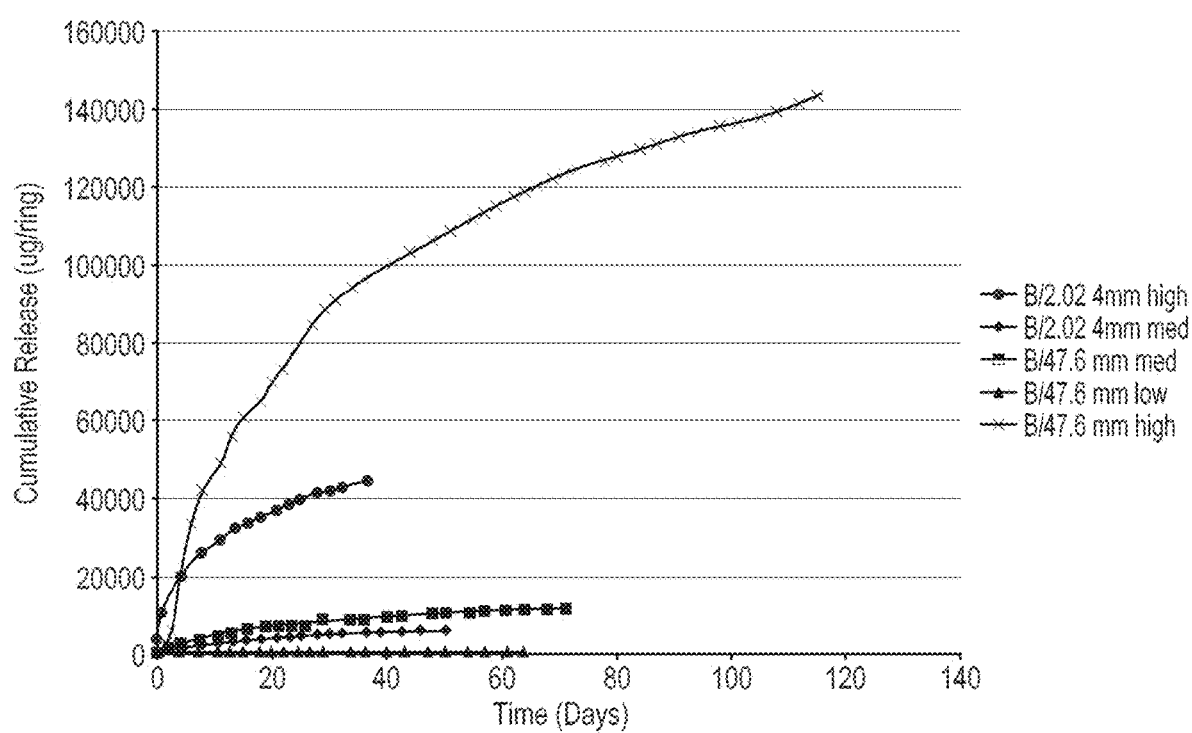
Figure 23B:
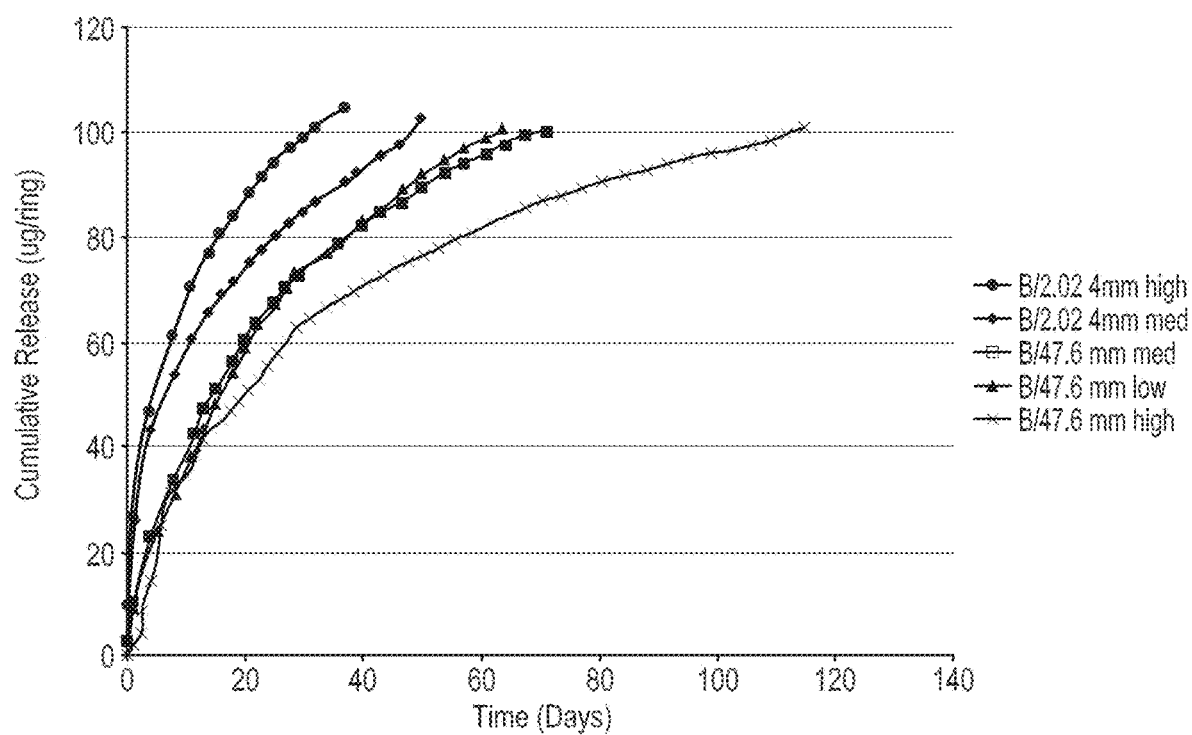

FIGS. 23A and 23B are graphical depictions of the results of cumulative drug released (FIG. 23A) and cumulative % drug released (FIG. 23B) of IVRs with different macroscopic architecture and loading.

Figure 24A:
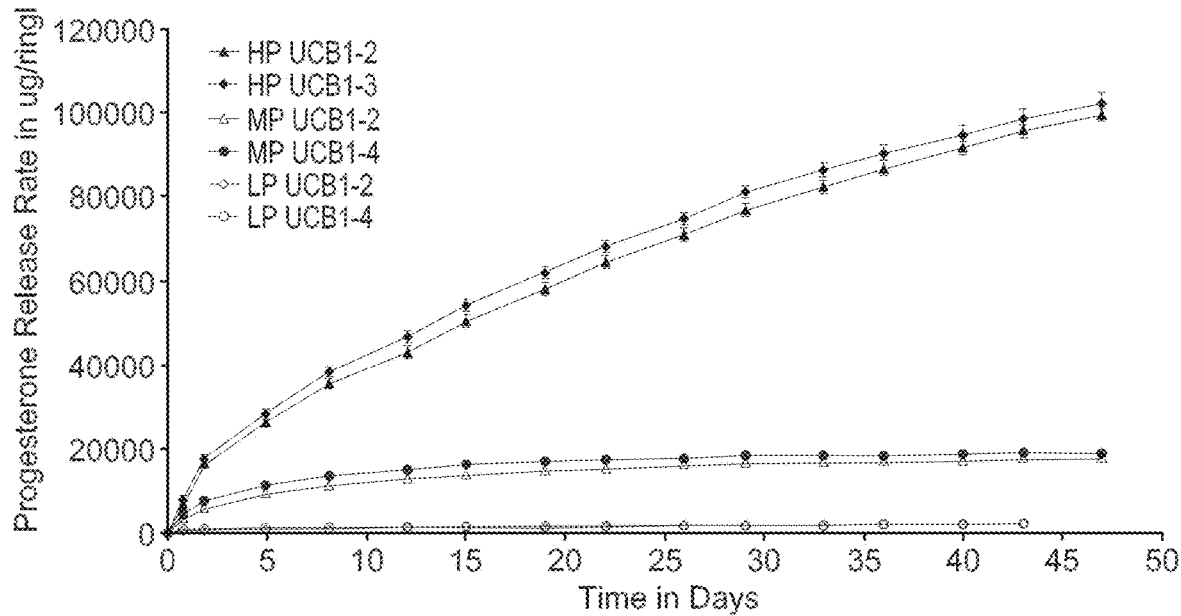
Figure 24B:
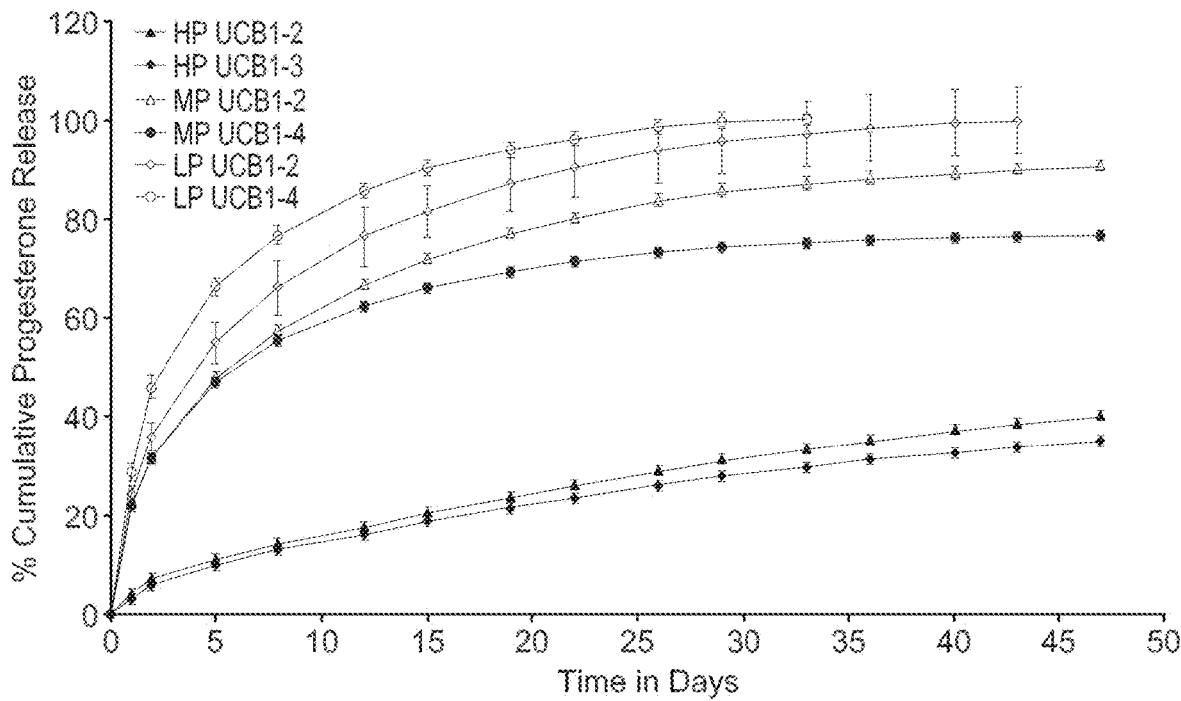

FIGS. 24A and 24B are graphical depictions of the results of testing for the release of progesterone from geometrically complex IVRs with a range of fractional volume and loading levels (FIG. 24A, ug/ring; FIG. 24B, %/ring) as a function of time in days.

DETAILED DESCRIPTION

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

The terminology used herein is for the purpose of describing particular embodiments only and is not intended to be limiting of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a unit cell" includes a plurality of such unit cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

Overview of the Presently Disclosed Subject Matter

Disclosed herein are geometrically complex intravaginal rings (IVRs) with tunable and enhanced drug release, which in some embodiments can be fabricated by 3D printing technologies. In some embodiments, disclosed herein are 3D printing technologies such as state of the art Continuous Liquid Interface Production (CLIP) technology to engineer new geometrically complex IVRs. With 3D printing technologies, IVRs can be engineered with controlled shape, size, volume, capacity, and surface area within the IVR, such as for example those IVRs illustrated in FIG. 4. These new complex geometries can be adjusted during fabrication and can be designed precisely to 1) fine-tune the release of drugs from the IVR, 2) develop IVRs that can release a drug for more than 30 days, 3) optimize drug loading in the IVR, and 4) integrate two or more drugs in a single IVR. In some embodiments this technology can provide a cost effective engineering process that can allow for the development of IVRs with customized designs to release two or more drugs at efficient release rates.

The IVRs can in some embodiments be used for the following applications: 1) HIV PrEP, 2) HIV treatment, 3) contraception, 4) prevention of other sexually transmitted diseases (STDs) such as Herpes Simplex Virus type 2, HPV, and other STDs, 5) treatment of infections such as urinary tract infections, cystitis, chlamydia and others, 6) treatment of diseases such as cancer (e.g. cervical cancer, ovarian cancer, uterine cancer and others), 6) hormone therapy, 7) collection of cervicovaginal lavage samples, 8) vaccine development (e.g. HPV and others), 9) women's health indications (e.g. preterm birth, infertility and others), 10) post-surgery or chemotherapy treatments, and/or 11) prevention or treatment of infectious diseases (bacterial, viral or other).

In some embodiments the disclosed geometrically complex IVRs fabricated by 3D printing technologies (e.g. CLIP) can provide superior control over drug loading and drug release compared to conventional IVRs fabricated by injection molding or hot-melt extrusion. In some embodiments fabrication of multipurpose IVRs with 3D printing processes can be significantly more cost efficient than injection molding or hot-melt extrusion. In some embodiments provided herein are methods and systems that provide for the structure, shape, and size design development for the fabrication of IVRs with loading and release characteristics specifically applicable to combination therapies that are not currently available, and that can be substantially more rapid compared to injection molding or hot-melt extrusion.

In some embodiments provided herein are 3D printed IVRs comprising a ring structure comprising a plurality of unit cells or macroscopic and/or microscopic architecture, wherein the unit cells, macroscopic architecture and/or microscopic architecture are configured to control the loading capacity of a compound within the IVR, the diffusion of a compound from the IVR, the surface area of the IVR, and/or the mechanical properties of the IVR. In some embodiments the IVRs are fabricated by 3D printing. In some embodiments the 3D printing process used in fabrication comprises CLIP. In some aspects the shape, size, and/or surface area within the IVR is produced by the 3D printing.

In some embodiments geometrically complex IVRs are provided, where the IVRs comprise a three dimensional ring structure. The ring structure can in some aspects comprise a body forming a circular, spherical or oblong structure, in some aspects a ring-like structure, having an inner diameter and an outer diameter. The body of the IVR can be made of a plurality of unit cells as defined herein. Such unit cells can comprise macroscopic and/or microscopic architecture forming geometric shapes and designs. Such unit cells can be designed to optimize and/or increase surface area and/or loading capacity, such that when combined together with a plurality of the same or differing unit cells the properties of the body of the IVR are dictated by the combined effect of the unit cells. In some embodiments, the macroscopic architecture and/or microscopic architecture of the unit cells can be configured to control a loading capacity of an active compound within the IVR, a diffusion rate of an active compound from the IVR, a surface area of the IVR, a fractional volume of the IVR, and/or a mechanical property of the IVR. By way of example and not limitation, and as discussed further herein, exemplary unit cells are shown in FIG. 4. In some aspects the disclosed IVRs can comprise one or more types of unit cells, wherein each type of unit cell varies in size, shape, configuration, surface area and/or three dimensional geometry.

Figure 4A:
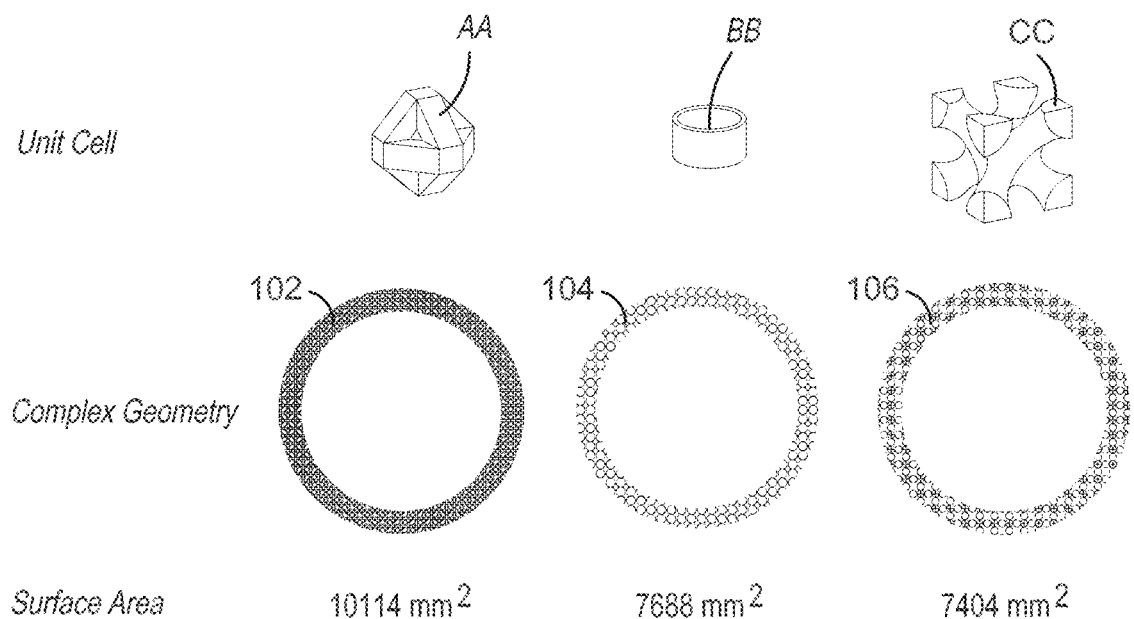
FIGS. 4A and 4B are illustrations of exemplary unit cell types.
Figure 4B:
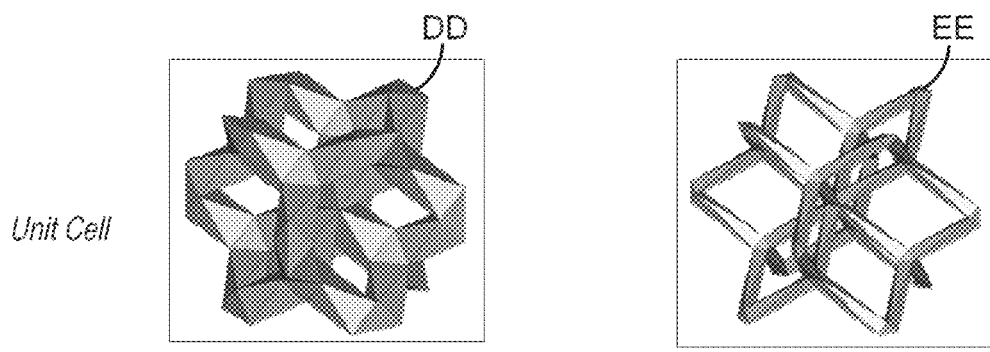

In some embodiments, a "unit cell" as used herein can comprise a three dimensional geometric shape or design generated by 3D printing, including for example those exemplary unit cells shown in FIGS. 4A and 4B (for example, unit cells AA, BB, CC, DD and EE). Moreover, in some embodiments a "unit cell" as disclosed herein can comprise any structure or building unit having a macroscopic and/or microscopic architecture forming a geometric shape or design, or an irregular shape or design, including those formed by methodologies other than 3D printing, including for example foaming or die-cut methods. Such unit cells can be used as building blocks to form the geometrically complex IVRs as disclosed herein. In some embodiments, the unit cells disclosed herein can range from about 0.1 mm to about 15 mm in one or more of three dimensions of X, Y and Z.

A geometrically complex IVR can in some aspects be defined as a structure containing void volumes within the IVR. Specifically, geometrically complex IVRs can have volume fractions less than one when compared to a solid IVR of the same outer diameter (O.D.) and cross-section (C.S.). Geometrically complex IVRs as disclosed herein can have volume fractions ranging from 0.1 to 0.9 when compared to their solid counterparts. In some aspects geometrically complex IVRs can have a void volume that is regularly or irregularly distributed continuously or in discrete volumes greater than or equal to about 10. In some embodiments, the geometrically complex IVRs disclosed herein can have an outer diameter, inner diameter, and/or a cross-section of the body of the IVR that is variable across the device. That is, the diameter and/or cross-sectional dimensions can vary throughout the three dimensional ring structure.

In some embodiments IVRs as disclosed herein, and particularly made up of a plurality of unit cells, can have a fractional volume of about 0.1 to about 0.9, optionally about 0.2 to about 0.8, or about 0.3 to about 0.7. As exemplified in the Examples below, in some embodiments the Volume Fraction can be calculated based on Equation 1:

$$\text{Geometric Complexity by Volume Fraction:} \frac{\text{Volume of } IVR \text{ with Void Spaces}}{\text{Volume of Solid } IVR} < 1, \quad \text{[Equation 1]}$$

with the loaded fractional volume being calculated based on Equation 2:

$$\text{Volume Fraction} \times \text{Loading.} \quad \text{[Equation 2]}$$

In some embodiments the IVRs are configured to enhance and/or control release of the compound. In some embodiments the IVRs are configured to control the rate and/or duration of diffusion of the compound from the IVR, wherein the compound can be released from the IVR for an extended period of time, optionally 1, 2, 3, 4, 5, 6, 7, 8, 9, 10, 15, 20, 25, 30, 35, 40, 45, 50 days or more.

In some embodiments the resin formulation can comprise an additive selected from the group consisting of a pore-forming agent, a plasticizer, a stabilizer, a filler and/or combinations thereof. In some embodiments the pore-forming agent comprises one or more of PEG 3000, PEG 6000, PEG 8000, hydroxypropyl cellulose, $PVP_{10000}$, and $PVA_{10000}$. In some embodiments the pore-forming agent is configured to create aqueous diffusion pathways for a drug molecule over time. In some embodiments the resin formulation comprises additives for the purpose of influencing drug solubility, viscosity, porosity, stability, or mechanical properties during processing or surface properties, swelling, stability, or mechanical properties during packaging, storage, or use. In some embodiments the IVRs are configured to release two or more compounds simultaneously or iteratively and at predetermined rates and durations.

In some embodiments the IVRs disclosed herein can comprise or be configured to release an active compound, active agent or therapeutic compound. Such active agents can comprise one or more of an antiviral, antiretroviral, microbicide, contraceptive, antibiotic, hormone, pre-exposure prophylaxis, small molecule drug, macromolecule drug (e.g. dendrimer), biopharmaceutical, chemotherapeutic, biologics (e.g. antibodies, peptides and other), or other pharmaceutical compound, and/or combinations thereof. In some aspects the IVRs provided herein are configured to release two or more active compounds simultaneously or iteratively and at predetermined rates and durations.

The active compound or compounds can be incorporated into the body of the disclosed IVRs during or after 3D printing. Alternatively, the active compound can be incorporated into the IVR after 3D printing by coating, absorption, infusion, or adsorption of active compound onto the IVR. Still yet, in some embodiments, IVRs disclosed herein can comprise a gel-like compound, wherein the gel-like compound is incorporated into the IVR after 3D printing by filling a void volume of the IVR. A gel-like compound can comprise a gel, that can in some embodiments be defined as a solid jelly-like material that can have properties ranging from soft to hard with varying degrees of viscosity. In some aspects, one or more active compounds can be captured inside one or more nanoparticles incorporated into the body of the IVR. In some instances the active compound in nanoparticles can be dispersed into a resin formulation from which the IVR, and/or the unit cells, is fabricated. In some embodiments the IVRs are configured for one or more of the following applications: HIV pre-exposure prophylaxis (PrEP), HIV treatment, contraception, prevention of other sexually transmitted diseases (STDs) such as Herpes Simplex Virus type 2, HPV, and other STDs, treatment of infections such as urinary tract infections, cystitis, chlamydia and others, treatment of diseases such as cancer (e.g. cervical cancer, ovarian cancer, uterine cancer and others), hormone therapy, collection of cervicovaginal lavage samples, vaccine development (e.g. HPV and others), treatment or prevention of infectious diseases (viral, fungal, bacterial and other), and women's health indications (e.g. preterm birth, fertility and others). In some embodiments the IVRs comprise one or more types of unit cells, wherein each type of unit cell varies in size, shape, configuration, surface area and/or three dimensional geometry.

In some embodiments provided herein are methods of fabricating a 3D printed IVR, comprising: providing a template for an IVR, the template comprising a ring structure comprising a plurality of unit cells, macroscopic architecture and/or microscopic architecture; providing a material from which the IVR is to be fabricated; providing a 3D printing system; and producing an IVR from the material using the 3D printing device based on the template. In some embodiments the methods comprise providing a therapeutic compound or active agent as disclosed herein, wherein the therapeutic compound is incorporated into and/or onto the IVR during or after 3D printing. In some embodiments the therapeutic compound comprises one or more of an antiviral, antiretroviral, microbicide, contraceptive, antibiotic, hormone, pre-exposure prophylaxis, small molecule drug, macromolecule drug (e.g. dendrimer), biopharmaceutical, biologics (e.g. antibodies, proteins, peptides), chemotherapeutic or other pharmaceutical compound, and/or combinations thereof. In some embodiments the unit cells are configured to control the loading capacity of a compound within or on the IVR, the diffusion of a compound from the IVR, the surface area of the IVR, and/or the mechanical properties of the IVR. In some embodiments the 3D printing system comprises a CLIP system.

With the CLIP process, and in some embodiments other 3D printing methods and systems, the rate of release of different drugs can be controlled through both chemistry and design. The CLIP process, and in some embodiments other 3D printing methods and systems, can also allow for the use of crosslinkable monomers or oligomers to fabricate IVRs with crosslinked networks. By varying the degree of crosslinking, IVRs with a specific range of swelling and diffusion behavior can be fabricated with the CLIP process. This is another way of tuning and controlling drug release from the IVR. Fabricating designs with complex geometries including a range of deliberately controlled open volume and surface area can in some embodiments also serve as a control parameter for the release rate of drugs and other actives.

Without being bound by any particular theory or mechanism of action, the efficacy of IVRs as long-acting delivery devices is dependent, at least in part, on their ability to remain in place for the duration of use. An elastic IVR under compression will be in a force balance with the vaginal wall. The magnitude of the force balance is determined by ring geometry, matrix material properties and the biomechanical forces attributed to the vaginal musculature. Provided the magnitude of the IVR retractile force is sufficient, the ring will remain in place [10]. Under normal physiological conditions, the vaginal tract is a low-friction environment due to the presence of vaginal fluid and cervicovaginal mucus. If an IVR is too easily deformed, the ring may be expelled as a result of day-to-day activities of the user such as defecation, sexual intercourse, or running [11]. On the other hand, if the retractile force is too large, it may result in difficulty for the user to apply the IVR and may cause damage to the vaginal epithelium proximal to the IVR [12, 13].

Based on a mechanical model for the point of compression of thin elastic rings, increasing the cross-sectional diameter of an IVR from 5 to 6 mm will result in a 107% increase in the force required to deform the ring by a given amount. Moreover, IVR compression is linearly related to the elastic modulus of the IVR matrix, which can be influenced by the incorporation of drugs and/or other excipients. For instance, the addition of non-dissolved solids to the matrix can greatly increase the elastic modulus, whereas dissolution of polymer-soluble compounds can cause a plasticizing effect and thereby reduces the elastic modulus of the material.

In some embodiments the physical and mechanical properties of the IVR are controlled by the light intensity, print time, print orientation, and other parameters during the 3D printing, the material used during 3D printing, and/or the degree of cross-linking during 3D printing. In some embodiments the IVR is generated to comprise one or more types of unit cells and/or macroscopic architectures and/or microscopic architectures, wherein each type of unit cell varies in size, shape, configuration, fractional volume, surface area and/or complex three dimensional geometry.

In some aspects, the shape, size, fractional volume, and/or surface area of the body of the IVR can be produced by a foaming method, for example where a foaming agent (e.g. chemical blowing agent or physical blowing agent) is incorporated into a polymer or pre-polymer formulation that is molded or extruded into a IVR shape prior to or in conjunction with a foaming step to form the geometrically complex IVR structure incorporating macroscopic and/or microscopic architecture and a fractional volume in the range of about 0.1 to 0.9. The geometrically complex IVRs disclosed herein can have the shape, size, fractional volume, and/or surface area of the body of the IVR produced by a die-cut method, for example where a IVR shaped die is used to remove geometrically complex IVRs from a foamed polymer sheet or film.

Provided herein are methods of fabricating IVRs, including 3D printed IVRs. Such methods can comprise, providing a template for an IVR, where the template can comprise a three dimensional ring structure comprising a plurality of unit cells, macroscopic architecture and/or microscopic architecture, and in some aspects a desired geometric complexity. Once a template is in place a material from which the IVR is to be fabricated can be selected, and an appropriate 3D printing system or methodology can be selected. An IVR with the desired geometric complexity can then be fabricated from the material using the 3D printing device based on the template.

In some aspects one or more active compounds can be selected based on the intended use or functionality of the IVR, and the active compound can be incorporated into the IVR during or after 3D printing. The active compound can be captured inside one or more nanoparticles incorporated into the IVR. Or, the active compound can be incorporated into the IVR after 3D printing by coating, absorption, infusion, or adsorption of active compound onto the IVR. Still yet, in some applications a gel-like compound can be incorporated into the IVR after 3D printing by filling a void volume of the IVR.

As discussed herein, the unit cells from which the IVR is constructed can be configured to control the loading capacity of an active compound within or on the IVR, the diffusion of the active compound from the IVR, the surface area of the IVR, and/or the mechanical properties of the IVR.

In the disclosed methods of fabricating IVRs, 3D printing systems can be employed, including for example a CLIP system. The shape, size, and/or surface area within the IVR can be produced by the 3D printing of the IVR. The physical and mechanical properties of the IVR can be controlled by light intensity, print time, print orientation, and/or other parameters during or after the 3D printing, the material used during 3D printing, and/or a degree of cross-linking during or after 3D printing. In some embodiments the IVR can be generated to comprise one or more types of unit cells, wherein each type of unit cell varies in size, shape, configuration, surface area and/or complex three dimensional geometry.

In some embodiments the methods further comprise a computer readable medium having stored thereon executable instructions that when executed by the processor of a computer control the computer to perform one or more of the steps. In some embodiments the computer readable medium having stored thereon executable instructions that when executed by the processor of a computer control the computer to generate a virtual three dimensional template of an IVR. In some embodiments the computer readable medium having stored thereon executable instructions that when executed by the processor of a computer control the computer to control a 3D printing device in communication with the computer, whereby the 3D printing device prints an IVR. In some embodiments the IVR template can comprise a standard tessellation language (STL) file, wherein the IVR template comprises an IVR with an outer diameter (O.D.) of about 3 mm to about 65 mm, or about 5 mm to about 55 mm, or about 10 mm to about 45 mm, or about 20 mm to about 35 mm, and cross-sectional diameter (C.S.) of about 0.5 mm to about 15 mm, or about 1 mm to about 10 mm, or about 2 mm to about 8 mm, wherein the IVR template comprises a unit cell selected and arrayed within the template to generate a geometrically complex part. In some embodiments the IVR template can comprise an STL file, wherein the IVR template comprises an IVR with different outer diameter dimensions in two or more dimensions ranging from about 3 mm to about 65 mm, or about 5 mm to about 55 mm, or about 10 mm to about 45 mm, or about 20 mm to about 35 mm, and different cross sectional diameters in two or more regions of the IVR ranging from about 0.5 mm to about 15 mm, or about 1 mm to about 10 mm, or about 2 mm to about 8 mm. In some embodiments the IVR template comprises an STL file, wherein the IVR template comprises an IVR with a patient-specific inner diameter and cross-sectional diameter, wherein a patient is selected from human, non-human primate, mouse or other mammal, wherein the IVR template comprises a unit cell selected and arrayed within the template to generate a geometrically complex part. In some embodiments the IVR template can be iteratively used to generate geometrically complex IVRs comprised of different unit cells. By way of example and not limitation, the unit cells can range from about 0.1 mm to about 15 mm in three dimensions of X, Y and Z.

In some embodiments, provided herein are methods of treating a subject, including female human subjects. Such methods can include providing a subject in need of treatment, providing a geometrically complex IVR as disclosed herein, and placing the IVR intravaginally in the subject, whereby the subject is treated. The IVR can be developed and/or selected to contain one or more active agents effective to treat one or more conditions or indications of the subject.

By way of example and not limitation, the active compound can comprise a therapeutic compound selected from an antiviral, antiretroviral, microbicide, contraceptive, antibiotic, hormone, pre-exposure prophylaxis, small molecule drug, macromolecule drug, biopharmaceutical, biologics, chemotherapeutic, other pharmaceutical compound, and combinations thereof. By way of example and not limitation, the subject may be in need of HIV pre-exposure prophylaxis (PrEP), HIV treatment, contraception, and/or prevention of sexually transmitted diseases (STDs), e.g. Herpes Simplex Virus type 2, HPV, and other STDs, treatment or prevention of infectious diseases, and other women health indications, e.g. preventing preterm or premature birth, treating infertility/promoting reproductive fertility, and others. In some aspects the subject might be in need of treatment of infections, optionally wherein the infections are selected from the group consisting of urinary tract infections, cystitis, and chlamydia. In some aspects the subject might be in need of treatment of diseases and cancers, optionally wherein the cancers are selected from the group consisting of cervical cancer, ovarian cancer and uterine cancer. In some aspects the subject might be in need of post-surgery or post-chemotherapy treatment.

As used herein, the terms "treating," "treatment", and "to treat" are used to indicate the production of beneficial or desired results, such as to alleviate symptoms, or eliminate the causation of a disease or disorder either on a temporary or a permanent basis, slow the appearance of symptoms and/or progression of the disorder, or prevent progression of disease. For methods of prevention, a subject using the disclosed IVRs is generally a subject at risk for a STDs, reproductive diseases, infections, and female health conditions. The term "treat" or "treatment" refer to both therapeutic treatment and prophylactic or preventative measures, wherein the object is to prevent or slow down the development or spread of disease or symptoms. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total). "Treatment" can also refer to prolonging survival as compared to expected survival if not receiving treatment.

In some embodiments the subject to be treated, or for which a IVR as disclosed herein is designed and/or formulated, is a female human subject. However, it is to be understood that the principles of the disclosed subject matter indicate that the devices, compositions and methods are effective with respect to invertebrate and to all vertebrate species, including mammals, which are intended to be included in the term "subject".

The term "subject", "individual", and "patient" are used interchangeably herein, and refer to an animal, especially a mammal, for example a human, to whom treatment, with a composition as described herein, is provided. The term "mammal" is intended to encompass a singular "mammal" and plural "mammals," and includes, but is not limited: to humans, primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears.

Moreover, a mammal is understood to include any mammalian species in which treatment is desirable, including for example research, agricultural and domestic mammalian species.

HIV Applications

Despite decades of research, at the end of 2014 an estimated 36.9 million people were living with HIV/AIDS and about 2.0 million people were newly infected globally [14]. Advances in antiretroviral therapy have reduced the morbidity and mortality associated with HIV/AIDS, however, this pandemic disease continues to spread worldwide. Thus, it is imperative that effective HIV prevention tools are developed and rapidly implemented. Mucosal HIV exposures through receptive anal and vaginal intercourse are responsible for the vast majority of HIV-1 infections [15]. The recent success of the CAPRISA 004 trial using vaginally applied Tenofovir (TFV) has fueled the interest in the use of topical antivirals for the prevention of HIV transmission [16]. Despite the highly encouraging results from the CAPRISA 004 trial, poor adherence to PrEP regimens has been implicated as a primary factor in determining efficacy of these trials. Therefore, there is a strong need to discover, test, and develop the next generation of PrEP agents and combination of agents with optimized properties capable of effectively preventing HIV acquisition by uninfected individuals.

Innovations recently introduced into the field of HIV PrEP are long-acting (LA) formulations of antiretrovirals that stably release drugs over many weeks either as nanocrystal-based-formulations for systemic delivery or intravaginal rings for topical delivery [7, 8]. These approaches offer major benefits mainly in the ability to mitigate poor patient adherence with daily tablet PrEP dosing.

Intravaginal Rings (IVRs)

With 51% of the individuals infected with HIV being women, there is a critical need to promote female-controlled methods of HIV/STI prevention and delivery strategies that can be disassociated from the sex act.

Examples of IVRs include a Phase 2a study of a Dapivirine ring for HIV prevention, a phase 1 study with a vicriviroc and MK-2048 combination IVR, and a Phase 1 study of a combination IVR releasing TFV and LNG for prevention of HIV and contraception [17]. There have been extensive studies now completed on the compliance of vaginal ring users that confirm strong acceptability and compliance [18-23]. Intravaginal rings are now commercially available as a contraceptive or estrogen delivery systems. However, these solid structure rings are made from either copolymers of EVA (e.g., NUVARING®) or silicone-based (e.g., ESTRING®) elastomers.

Unfortunately, existing IVRs require multiple steps and in some cases, the use of multiple polymer components to manufacture the final IVR. The multiple process steps required for IVR fabrication limits the scalability of these IVRs in a time and cost efficient process. In addition, the process used to fabricate existing IVRs utilizes either hot-melt extrusion or injection molding and requires at least 3 or 4 steps to produce the final IVR product. Moreover, fabrication of IVRs by injection molding and hot-melt extrusion requires 1) drug to be miscible in the melted polymer, 2) drug to be stable and not phase separate once the IVR is cooled to room temperature, and 3) drug to be stable under the manufacturing conditions (120° C. and 90 psi for injection molding, 150-160° C. for hot-melt extrusion). These high temperatures are required to induce flow in the starting material, which is a high molecular weight polymer.

In contrast, in the CLIP process, and some other 3D printing methods, because the starting resin flows as a liquid at room temperature, high temperatures are not necessarily a requirement to fabricate IVRs.

Moreover, the most recent Phase 1 clinical study with a matrix silicone IVR containing Dapavirine and Maraviroc individually or in combination showed that the single rings had more stable pharmacokinetics resulting in better efficacy against HIV transmission compared to the combination drug IVR [24]. It is therefore evident that there is a need to improve on the current technologies in order to develop a safe, cost effective, and efficient IVR for HIV PrEP and for prevention of unwanted pregnancies and other STDs.

3D Printing Technologies 3D printing, also known as rapid prototyping or additive manufacturing, can be described as a process by which a part, defined from a computer-aided design (CAD) file, is generated, traditionally, in a layer-by-layer fashion. Compared to conventional plastic molding manufacturing processes like injection molding and extrusion, 3D printing provides a plethora of design freedom and enables relatively rapid fabrication of customized objects with complex geometries. One advantage of 3D printing is the ability to directly translate a concept design into an end product in a convenient, cost efficient manner. 3D printing also provides the opportunity to produce parts and components made of different materials with adjustable mechanical and physical properties. However, one limitation of some current 3D printing processes such as fused deposition modeling (FDM) selective laser sintering (SLS), and stereolithography (SLA) is that the resolution and mechanical integrity of the products can be poor related to the fact that these methods rely on a layer-by-layer printing process which induces anisotropy and interfacial stresses into the product on a fine scale. For 3D printing to be viable in mass production, print speeds must significantly increase while maintaining part accuracy and mechanical integrity.

As provided herein, 3D printing technologies that can be utilized to fabricate geometrically complex IVRs include but are not limited to: stereolithography, multijet modeling, binder jet technique, fused deposition modeling (FDM) or fused filament fabrication (FFF), selective laser melting (SLM), selective laser sintering (SLS), digital light processing (DLP), top-down SLA DLP, intelligent liquid interface (ILI) using wettable membrane technology, powder bed and inkjet head 3D printing (3DP), electron-beam melting (EBM), selective heat sintering (SHS), stereolithography (SLA), and continuous liquid interface production (CLIP). In some embodiments herein the fabrication of geometrically complex IVRs can be by the CLIP process, but other 3D printing technologies can also be used to fabricate IVRs and are equally applicable to the various embodiments of the instant disclosure.

Continuous Liquid Interface Production (CLIP)

Continuous liquid interface production of 3D objects is an innovative 3D manufacturing process whereby complex objects can be produced in minutes, instead of hours which is more typical of alternative 3D printing processes [25]. CLIP can be achieved using an oxygen-permeable window below the ultraviolet image projection plane, creating what is know as a "dead zone" at the window/resin interface. Within the dead zone, photopolymerization is inhibited in a controlled fashion between the window and the polymerizing part [25]. CLIP is a continuous and 'layerless' process, meaning that there is no need to separate the part from the window and re-apply resin between projected images, drastically decreasing the overall print time compared to alternative 3D printing techniques. As with other 3D printing techniques, CLIP allows rapid production of parts with complex geometries and microscopic features.

In the case of ambient air below the oxygen-permeable window, the dead zone thickness is dependent on: a) the incident photon flux (i.e. light intensity, $\Phi_0$), photoinitiator absorption coefficient ($\alpha_{PI}$), resin absorption coefficient ($\alpha$), and resin curing dosage ($D_{c0}$) according to equations 4 and 5 [25].

$$\text{Dead zone thickness} = C\left(\frac{\Phi_{0\alpha PI}}{D_{co}}\right)^{-0.5} \quad \text{[Equation 4]}$$

Where C is proportionality constant.

$$\text{Cured thickness} = \frac{1}{\alpha}\ln\left(\frac{\Phi_{0\alpha PI} t}{D_{co}}\right) \quad \text{[Equation 5]}$$

Where t is exposure time.

The continuous nature of the CLIP process can in some embodiments allow for the manufacturing of smooth and precise 3D objects with no model slicing artifacts seen in some 3D printing systems that use layer-by-layer approaches. DeSimone et al. demonstrated the ability to manufacture parts with fine detail with CLIP even in the microscopic dimension range. Using the CLIP process, complex solid parts can be grown out of the resin pool at rates of hundreds of millimeters per hour. These print speeds allow parts with complex geometries to be fabricated in minutes instead of hours [25].

However, higher resolution of small features and smoother angled surfaces can, in some embodiments, be obtained using CLIP as there is no trade off between resolution and the number of projected images using CLIP, and a higher number of projected images leads to greater resolution. In addition, a 3D printing process would be most cost effective on the industrial scale if it were able to produce a part very rapidly. The CLIP platform integrates polymer synthesis and part fabrication in a single step thus allowing for the exploration of alternative materials and designs including complex geometries that would otherwise be excluded from the conventional device manufacturing technologies (i.e. injection molding, hot-melt extrusion). This is particularly advantageous for design and fabrication of multipurpose IVRs.

Utilizing the unique advantages of the CLIP process to fabricate intravaginal rings with complex geometries opens an era of design freedom that is not provided by current manufacturing processes like injection molding and extrusion. Engineering IVRs with complex microscopic and/or macroscopic geometries, as disclosed herein, can allow control over drug loading and drug release and expand the formulation options to meet dose requirement for HIV PrEP.

The subject matter disclosed herein can be implemented by software in combination with hardware and/or firmware. For example, the subject matter described herein can be implemented in software executed by a processor. In one exemplary implementation, the subject matter described herein can be implemented using a computer readable medium having stored thereon computer executable instructions that when executed by a processor of a computer control the computer to perform steps. Exemplary computer readable mediums suitable for implementing the subject matter described herein include non-transitory devices, such as disk memory devices, chip memory devices, programmable logic devices, and application specific integrated circuits. In addition, a computer readable medium that implements the subject matter described herein can be located on a single device or computing platform or can be distributed across multiple devices or computing platforms.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Materials and Methods

Environmental Scanning Electron Microscopy (ESEM)

An Environmental Scanning Electron Microscope (ESEM) with an FEI Quanta 200 field emission gun was utilized to obtain micrographs of the fabricated parts. Cross-sectional segments of the geometrically complex IVRs were prepared by freezing the IVR in liquid $N_2$ and slicing the part with a razor to expose the internal structure.

An ESEM with an FEI Quanta 200 field emission gun was utilized to obtain micrographs of the fabricated parts. Geometrically complex IVRs were sectioned at 30° increments, resulting in 12 sections. Sections were imaged individually under low voltage condition.

Fluorescence Microscopy

An Olympus BX61 upright wide field fluorescent microscope was utilized to visualize the rhodamine-B loaded CLIP IVRs. The same cross-sectional parts imaged using ESEM were viewed for fluorophore distribution using an excitation wavelength of 553 nm.

M1 Printing Method for IVRs

The prepared resin was placed into the M1 (Carbon CLIP Printer) window cassette. The .stl file was loaded into the M1 software for printing. Single and double IVR .stl files were utilized in these studies. The IVR was printed in approximately 4 to 10 minutes depending on the resin and design features. The printed IVR was removed from the platform, soaked in stirring 2-propanol (IPA) for 30 seconds and blown dry using forced air to remove residual resin and solvent. The process was repeated to produce at least four replicate samples for drug release testing and at least 3 replicate samples for radial compression testing. Further post-processing conditions were resin dependent.

Radial Compression Method for IVRs

The force at 10% radial compression was measured using an Instron 5566 Universal test system and a 100N load cell. Tensile grips fitted with spacers to surround and support the upper and lower portion of an IVR without applying pressure to the ring seated in the fixtures were used for the testing. Once seated in the fixture, compression was applied to the IVR in the Z direction at 1 mm/s until the IVR had been compressed to a distance of 25% of its outer diameter. The load applied at 10% compression was measured as the force of the IVR at 10% radial compression (F10). F10 is reported in Newtons (N) as an average of 3 replicates unless otherwise noted.

In Vitro Release Studies

In vitro release of drugs into a simplified simulated vaginal fluid (SVF) were carried out on 3D-printed CLIP IVRs (N=4 unless otherwise stated). The SVF was adapted from Owen and Katz and consisted of 25 mM sodium acetate buffer (pH 4) plus 2% Solutol (Kolliphor HS 15) [26]. For all in vitro studies with human size IVRs, the IVRs were placed in straight-sided glass jars containing 200 mL SVF at 37±2° C. For in vitro studies with mouse size IVRs, IVRs were placed in 20-mL scintillation vials containing 10 mL of SVF at 37±2° C. Aliquots (1 mL) of the release medium were removed at specified time intervals and the release medium was replaced completely with 200 mL of fresh SFV twice per week to maintain sink conditions.

High-Performance Liquid Chromatography (HPLC)

A reverse-phase HPLC method was developed and validated to quantify the concentration of drug(s) released in vitro from prototype IVRs fabricated with the CLIP process. The HPLC analysis was carried out with a Finnigan Surveyor HPLC system (Thermo Finnigan, San Jose, California, United States of America) with a Photodiode Array (PDA) Plus Detector, auto-sampler, and LC Pump Plus. The stationary phase utilized for the analysis was a Inertsil ODS-3 column (5 µm, 4.6×150 mm, [GL Sciences, Torrance, CA]) maintained at 40° C. Chromatographic separation was achieved by gradient elution using a mobile phase consisting of 0.1% trifluoroacetic acid in water and acetonitrile (ACN) (H$_2$O/ACN 95:5 v/v). The flow rate was 1.0 mL/minute and the total run time was 25 minutes for each 25 µL injection.

Example 1

Evaluating Geometric Complexity

A geometrically complex intravaginal ring (IVR) is defined as a structure containing void volumes within the IVR. Specifically, geometrically complex IVRs have volume fractions less than one when compared to a solid IVR of the same outer diameter (O.D.) and cross-section (C.S.), as shown in Equation 1.

$$\text{Geometric Complexity by Volume Fraction:} \frac{\text{Volume of } IVR \text{ with Void Spaces}}{\text{Volume of Solid } IVR} < 1 \qquad [\text{Equation 1}]$$

Volume of IVRs can be measured using conventional volume displacement measurements. Alternatively, the volume can be calculated from the mass of the part and the density of the material used in fabrication. The volume of a solid IVR of specified O.D. and C.S. can be determined by rendering in computer-aided design (CAD) software, empirically determined using volume displacement measurements, or calculated through geometric measurements of O.D. and C.S.

Figure 1A:
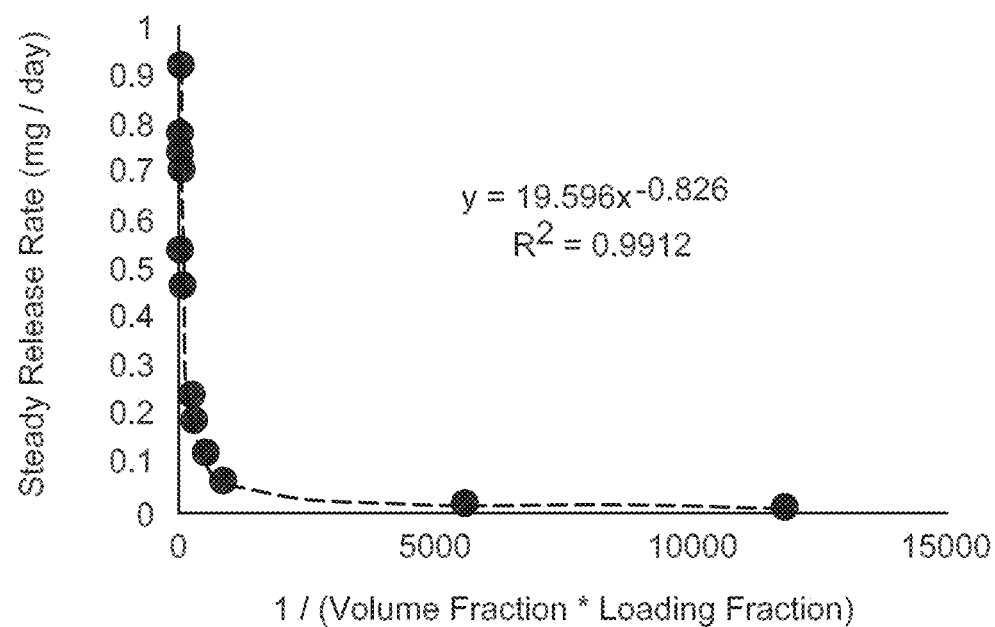
FIGS. 1A and 1B are plots of the inverse of the loaded volume fraction plotted as a function of the release rate for two different drug/resin IVR combinations, including the release rate of β-Estradiol loaded FPU 230 based IVRs (FIG. 1A) and Progesterone loaded PEG based IVRs (FIG. 1B).
Figure 1B:
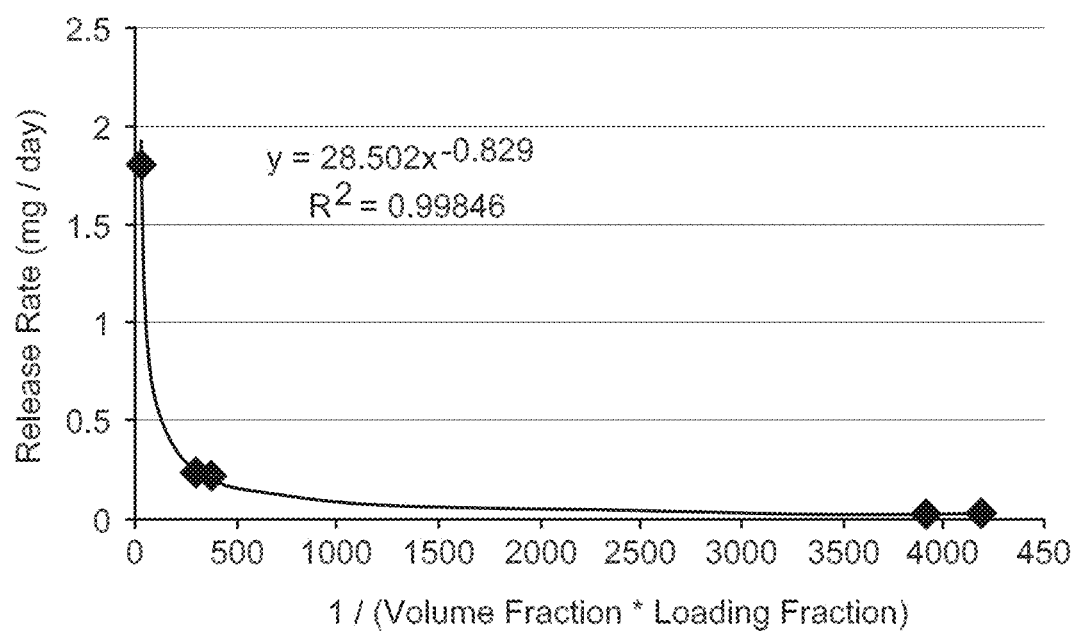

Geometrically complex IVRs disclosed herein have measured volume fractions in the range of 0.4 to 0.7. Loaded volume fraction is calculated as:

$$\text{Volume Fraction} \times \text{Loading} \qquad [\text{Equation 2}]$$

resulting in a unitless number. The inverse of the loaded volume fraction was calculated and plotted as a function of steady release rate, as shown in FIGS. 1A and 1B for both β-Estradiol loaded FPU 230 IVRs (FIG. 1A) and Progesterone loaded PEG based IVRS (FIG. 1B).

The data yields power functions for the case of UC-B β-Estradiol loaded FPU 230 as well as UC-B Progesterone loaded PEG showing that the function is largely dictated by the geometry of the rings driving the release rate with the drug and the resin determining the scaling. The release rate can be related to IVR geometric complexity through a power function taking the form $y=Cx^{-A}$ where:

$$\text{Release Rate} = C \times \text{Inverse Loaded Volume Fraction}^{-A}. \qquad [\text{Equation 3}]$$

Both examples yield a negative fractional power function where x represents a unitless value of 1/(volume fraction× loading) and y represents the release rate. The volume fraction is a function of the geometric complexity of the ring. The constants are a function of design and drug and resin interaction such that the exponent term (A) is primarily a function of design and the scaling factor (C) is a function of diffusion and drug distribution within the IVR.

Example 2 i. Prototype Intravaginal Rings (IVRs) Fabricated Using the CLIP Process

Prototype IVRs can be fabricated using the CLIP process at 1) multiple dimensions (human size IVRs and mouse size IVRs), with 2) a range of mechanical properties (bendability as a function of photon flux), and 3) different unit cells (generated by CAD files). As illustrated in FIGS. 2A through 2F, a human size IVR and a mouse size IVR with complex inner geometry were successfully fabricated using unit cell AA with the CLIP process. FIG. 2A is a photograph of a conventional human size matrix IVR (55 mm outer diameter (O.D.), 5 mm cross sectional diameter (C.S.)) fabricated by injection molding. FIG. 2B is a photograph of a human size IVR with complex inner geometry fabricated with CLIP (55 mm O.D., 5 mm C.S.). FIG. 2C is a mouse size IVR with complex inner geometry fabricated with CLIP (3 mm O.D., 1 mm C.S.). Corresponding IVR CAD files are illustrated in FIGS. 2D through 2F.

The human size IVR has a 55 mm outer diameter (O.D.) and a 5 mm cross-section (C.S.). The mouse size IVR has a 3 mm O.D. and a 1 mm C.S. This data demonstrates the ability to fabricate IVRs in a range of sizes using the CLIP process, while maintaining the integrity of the repeating complex geometrical structure within the IVR. This allows for preclinical studies to be conducted in mouse models and in non-human primate model to evaluate the efficacy of the IVRs for treatment applications, such as but not limited to sexually transmitted infections (STIs) such as HIV, herpes simplex virus type 2 (HSV-2), and others as well as unwanted pregnancies (i.e. contraception).

In some embodiments, multiple drugs can be formulated within the same IVR in a controlled and time efficient process. Choosing a resin that is suitable for solubilizing or dispersing multiple drugs (e.g. antiretroviral drugs, contraceptive drugs, microbicides, etc.) can allow for the fabrication of an IVR that contains multiple drugs as a multipurpose prevention technology (MPT) (e.g. prevention against STDs and unwanted pregnancies) [27]. Moreover, various monomers or oligomers that can be copolymerized can be used to fabricate a single IVR. This unique feature can allow two or more drugs to be co-formulated in a single IVR in a time efficient single step process. Based on the solubility and concentration of each drug in each monomer solution, drug loading and drug release from the IVR can be controlled. Additional methods of loading could disperse captured active agents inside nanoparticles into the resin formulation, thereby differentiating the distribution and release rate of the nanoparticle encapsulated active agent.

ii. Effect of Print Orientation on IVRs

One other factor in 3D printing and the CLIP process is the print orientation. It has been shown that the printing direction (horizontal vs. vertical) can influence the mechanical properties such as the compressive strength of printed parts [28]. The orientation used in the fabrication of the geometrically complex IVRs disclosed herein was one where the ring structure is parallel to the build platform, however, alternative orientations would also be applicable. For the fabrication of Part A (FIG. 7), the fractional UV intensity of the exposure was modified in the software to be 1.0, 0.8, and 0.6 equating to light intensities of 5.75, 4.60, and 3.45 mW/cm², respectively. Light intensity was measured using a Dymax AccuCal™ by Dymax Corporation at 3 mm aperture in Light Intensity mode. Part B and Part C (FIG. 3) were fabricated at full UV intensity of 5.75 mW/cm². All parts were fabricated at a build speed of 50 mm/hr.

Example 3 i. Computer-Aided Design (CAD) of IVRs by Varying Unit Cell

Prototype IVRs with different unit cells were generated using computer-aided design (CAD) files. Geometrically complex parts can be designed (FIG. 4). As shown in FIG. 4, three human size IVR prototypes (O.D. 55 mm, C.S. 5 mm) were generated with a range of surface areas (10114 mm², 7688 mm², and 7404 mm²). By using CAD, IVRs (or complex matrices) 102, 104 and 106, as shown in FIG. 4, were manufactured using unit cells AA, BB and CC, respectively. By varying the unit cell type from which each was built, the matrix properties and inner features can be varied, including for example the specific surface area of each, as shown in FIGS. 4A and 4B.

Figure 5:
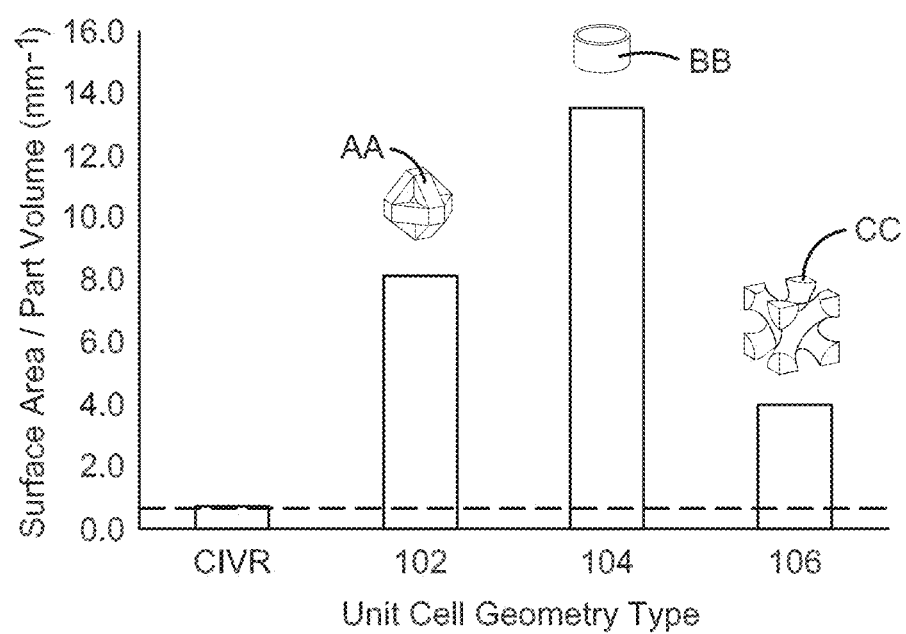
FIG. 5 is a histogram comparing the surface areas of conventional matrix IVR (CIVR) to CAD generated IVRs.

This is the first report of 3D printed IVR prototypes with varying surface area and unit cell dimensions. Drug loading within the IVR and drug release from the IVR are two parameters that can drive the success of IVRs for sustained drug delivery. Demonstrated herein is the method to design IVRs with tunable and controlled specific surface area (SAN, V=volume) (FIGS. 4 and 5). Given that drug-diffusion is influenced by IVR dimensions (i.e. cross-sectional diameter, C.D.) and surface area (SA), the method to produce prototype IVRs with controlled complex features and dimensions provides a unique opportunity to fine-tune drug release properties. Moreover, the comparison of a conventional solid matrix IVR versus CAD engineered IVRs shows that the overall specific surface area of IVRs engineered using a CAD file is significantly higher than a conventional matrix IVR (FIG. 5). The enhanced part specific surface area of CAD IVRs can correlate directly to higher drug diffusion compared to a conventional matrix IVR.

FIG. 5 shows the dimensional comparison of conventional matrix IVR (CIVR) to CAD generated IVRs 102, 104 and 106. FIG. 5 compares, from left to right, CIVR (O.D. 55 mm, 5 mm C.S.), CAD IVR 102 with hexagon unit cell AA (55 mm O.D., 5 mm C.S.), CAD IVR 104 with cylindrical unit cell BB (55 mm O.D., 5 mm C.S.), and CAD IVR 106 with cubical unit cell CC (55 mm O.D., 5 mm C.S.). IVRs with complex geometries, e.g. IVRs 102, 104 and 106, exhibit a much greater and design dependent specific surface area compared to a conventional matrix IVR.

FIG. 6 summarizes exemplary CAD IVR designs and nomenclatures used in the in vitro studies described herein.

ii. IVRs Fabricated with Varying Unit Cell

Figure 3A:
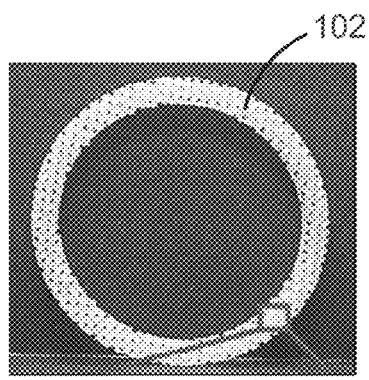
FIGS. 3A through 3F are environmental scanning electron microscopy (ESEM) images of prototype IVRs fabricated with varying unit cell properties.
Figure 3C:
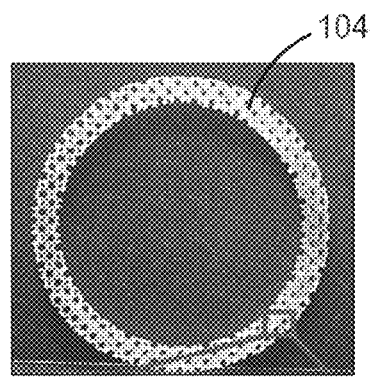
Figure 3E:
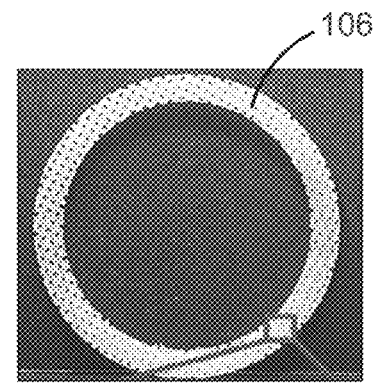
Figure 3B:
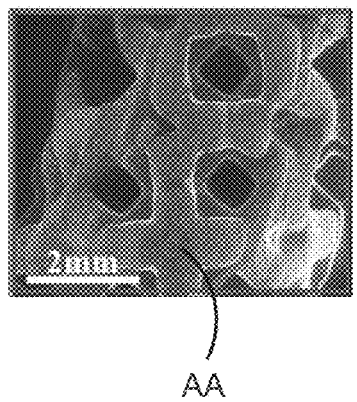
Figure 3D:
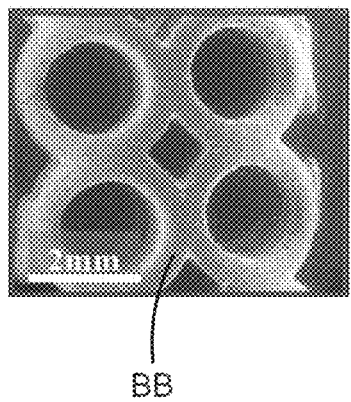
Figure 3F:
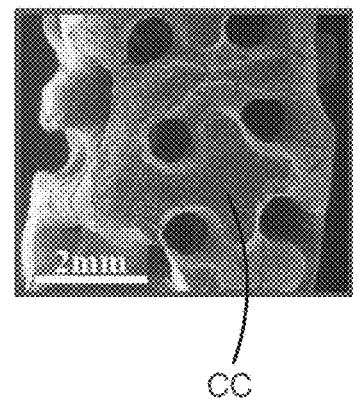

Using CAD files, IVRs were fabricated with varying unit cells (FIGS. 3A through 3F). This is the first report showing the ability to manufacture IVRs with varying unit cell properties and controlled complex geometries. FIGS. 3A, 3C and 3E are images of IVRs 102, 104 and 106, respectively, each of which was manufactured with varying unit cells as shown in the corresponding close-up images of FIGS. 3B, 3D and 3F. Using ESEM analysis, a cross-section view of IVRs fabricated with varying unit cells AA (FIG. 3B) BB (FIG. 3D) and CC (FIG. 3F) shows that the specific surface area can be tuned with the input unit cell and rapidly fabricated using CLIP. Complex geometries within an IVR allow interplay between drug loading (i.e. IVR volume) and drug release (i.e. IVR surface area). The shape and size of the complex geometries can be controlled by changing the CAD file to fine-tune drug loading and drug release properties from the IVR. By varying the dimensions of the unit cells within an IVR, drug diffusion properties can be varied and thereby drug release from the IVR. This is a feature unique to the 3D printing process, and that is not possible with classical manufacturing processes like injection molding and hot-melt extrusion. Additionally, resin formulation also plays a critical role in determining drug release properties based on the crosslinking density of the final IVR.

Example 4

Dual-Loaded IVRs

A prototype dual-loaded IVR was fabricated with the CLIP process using a hydrophobic resin loaded with R-250 (blue in color) and a hydrophilic resin loaded with Rhodamine B (red in color). The hydrophobic resin comprised of the following: methyacryloxypropyl terminated polydimethylsiloxane (Mn=380-500), methyacryloxypropyl terminated polydimethylsiloxane (Mn=900-1200), isobornyl methacrylate, ethyl (2,4,6-trimethyl benzyol) phenylphosphinate. The hydrophilic resin comprised of the following: poly(ethylene glycol) diacrylate (Mn=575), Poly(ethylene glycol) diacrylate (Mn=700), ethyl (2,4,6-trimethyl benzyol) phenylphosphinate, 2-(3'-tert-butyl-2'-hydroxy-5'-methylphenyl)-5-chlorobenzotriazole. The resulting 3D printed dual IVR with Rhodamine-B (red color) and R-250 (blue color) was purple, which indicated mixing of hydrophobic and hydrophilic resins during the fabrication process. This illustrates the ability to fabricate hydrophilic and hydrophobic compounds in a single IVR.

Also provided herein are methods to fabricate IVRs using a single resin loaded with two different classes of drugs, one antiretroviral drug (TDF), and one hormone drug (β-Estradiol) (Table 1). A series of IVRs were fabricated incorporating β-estradiol (ET) and tenofovir disoproxil fumarate (TDF) using the M1 printer as described in example 2. The resin was prepared by solubilizing both drugs in premixed FPU 230 in a Thinky ARE310 mixer for 10 minutes at 2000 rpm. A series of IVRs were fabricated on the M1 using the B unit cell design with a 54 mm outer diameter, 7.6 mm cross-section and 0.5 mm band thickness on the inner and outer diameters. IVRs containing 2, 3, and 4 unit cells across the cross-section were fabricated. Rings were washed in 100 mL of 2-propanol for 30 s followed by drying by compressed air. Rings were then treated to a thermal cure in a Yamato DKN602C constant temperature oven for 4 hours at 120° C. The IVRs were exposed to in vitro release in simulated vaginal fluid (SVF) as described above. The loading and release characteristics of the dual drug loaded IVRs are provided in Table 1. These data establish that multiple drugs can be loaded and released at tunable rates from geometrically complex IVRs.

TABLE 1

Dual drug loaded geometrically complex IVRs containing β-estradiol (ET) and tenofovir disoproxil fumarate (TDF).

| Sample | Fractional Volume | Loading TDF (mg/ring) | Loading ET (mg/ring) | Release TDF (μg/day) (days 4-28) | Release ET (μg/day) (days 4-28) |
|---|---|---|---|---|---|
| B/2 | 0.46 | 0.489 | 6.58 | 0.39 | 68 |
| B/3 | 0.54 | 0.300 | 8.26 | 0.55 | 99 |
| B/4 | 0.60 | 0.174 | 12.20 | 0.38 | 154 |

Example 5

Assessment of Mechanical Properties of IVRs i. Environmental Scanning Electron Microscopy (ESEM) of IVRs Fabricated at a Range of Light Intensity Environmental scanning electron microscopy (ESEM) analysis shows that the IVR fabricated at the highest light intensity (5.75 mW/cm$^2$) had more uniform inner features compared to the IVR fabricated at the lowest light intensity (3.45 mW/cm$^2$) (FIGS. 7A through 7F).

Prototyping resin 2.1 for the CLIP apparatus, obtained from Carbon3D, includes a proprietary mixture based on a diacrylated polyurethane oligomer and photo-initiator. Rhodamine B, purchased from Sigma Aldrich, was loaded at 0.01 wt. % into the resin using a Thinky Centrifugal mixer for 5 min at maximum speed. IVRs were fabricated using CLIP equipment supplied by Carbon3D containing a LED UV light source. The effect of light intensity (photon flux) on the physical and mechanical properties of the IVRs was investigated. IVRs with a range of mechanical properties were generated by varying the light intensity (photon flux) used in the CLIP process. In the CLIP process, increasing the photon flux resulted in increased concentration of free radicals in the resin and thereby increased rate of polymerization. The increase in the rate of polymerization can result in polymers with higher conversion at a given build speed and increased rigidity due to increased crosslink density. This explains the fact that IVRs fabricated at the lowest light intensity (3.45 mW/cm$^2$) exhibited the highest bendability properties. On the other hand, the IVRs fabricated at the highest light intensity exhibited the lowest bendability properties due to increased polymer conversion and crosslink density.

FIGS. 7A through 7F are ESEM images of prototype IVRs fabricated with varying light intensity (photon flux) using the CLIP process, which shows the effect of photon flux on inner geometry and mechanical properties. FIG. 7A shows an IVR fabricated at high light intensity (5.75 mW/cm$^2$), with a close-up view shown in FIG. 7B. FIG. 7C shows an IVR fabricated at medium light intensity (4.60 mW/cm$^2$), with a close-up view shown in FIG. 7D. FIG. 7E shows an IVR fabricated at low light intensity (3.45 mW/cm$^2$), with a close-up view shown in FIG. 7F.

This phenomenon can be attributed to the greater degree of polymerization obtained at higher light intensity whereby the polymer chains generated with a higher photon flux have higher crosslink density (Mc) and a more uniform molecular weight distribution resulting in a more uniform unit cell within the IVR.

ii. Radial Compression Testing

The design and material of IVRs affected the mechanical properties. F10 (force at 10% radial compression) has been used to estimate the load applied by an IVR in situ [29]. F10 is a force of relevance to IVRs as in vivo assessment of IVRs has measured an analogous compression of approximately 10% of 54 mm O.D. rings when they are in position in the vagina [29, 30]. Results are provided in Table 2 for radial compression force values (F10) measured for a variety of 3D printed IVRs including complex geometries and design features and made from a range of different materials. F10 values of injection molded solid controls are provided for comparison.

TABLE 2

| Unit Cell (UC) Design | Number of UC arrayed across the cross section | Additional Design Features | Cross section Diameter (mm) | Material | F10 (N) |
|---|---|---|---|---|---|
| Solid Control | n/a | None | 4 | Ethylene Vinyl Acetate (EVA) | 0.59 |
| BB | 2 | None | 4 | FPU 230 | 0.53 |
| BB | 3 | None | 4 | FPU 230 | 0.65 |
| BB | 4 | None | 4 | FPU 230 | 0.75 |
| BB | 2 | 0.3 mm thick band on ID and OD | 4 | FPU 230 | 2.15 |
| BB | 3 | 0.3 mm thick band on ID and OD | 4 | FPU 230 | 2.08 |
| BB | 4 | 0.3 mm thick band on ID and OD | 4 | FPU 230 | 1.89 |
| Solid Control | n/a | None | 7.6 | Silicone LSR 4350 | 0.77 |
| Solid Control | n/a | None | 7.6 | Silicone LSR 4330 | 0.41 |
| BB | 2 | None | 7.6 | FPU 230 | 4.36 |
| BB | 3 | None | 7.6 | FPU 230 | 6.09 |
| BB | 4 | None | 7.6 | FPU 230 | 5.69 |
| BB | 2 | 0.5 mm thick band on ID and OD | 7.6 | FPU 230 | 18.63 |
| BB | 3 | 0.5 mm thick band on ID and OD | 7.6 | FPU 230 | 18.95 |
| BB | 4 | 0.5 mm thick band on ID and OD | 7.6 | FPU 230 | 18.53 |
| BB | 3 | 0.5 mm thick band on ID and OD | 7.6 | EPU 60 | 1.17 |
| BB | 3 | 0.5 mm thick band on ID and OD | 7.6 | PDMS/PU | 0.27 |
| DD | 2 | None | 7.6 | FPU 230 | 6.21 |
| DD | 1 | None | 7.6 | FPU 230 | 4.00 |
| DD | 2.6 | 0.5 mm thick band on ID and OD | 7.6 | FPU 230 | 13.00 |
| DD | 2.6 | None | 7.6 | FPU 230 | 6.60 |
| EE | 2.6 | 0.5 mm thick band on ID and OD | 7.6 | FPU 230 | 6.91 |
| EE | 2.6 | None | 7.6 | FPU 230 | 2.68 |

The radial compression results establish that F10 is a function of material, size, and design. FIG. 13 compares 3D printed IVRs with the same complex design based on the BB unit cell arrayed three times across the 7.6 mm cross section including a band on both the inner and outer diameter of the IVR, shown as Design B in FIG. 6. The first three bars are the same complex design printed from three different materials (EPU 60, PDMS/PU, and FPU230). The last two bars (silicone solid control A, and silicone solid control B) are solid design silicone elastomers with the same cross section diameter of 7.6 mm. The same 3D printed IVR design, made of three different materials, have significantly different force values, some of which fall in the range of the solid IVR control samples.

FIG. 14 compares IVRs made using FPU 230 and the same unit cell and same added design feature with different numbers of unit cells arrayed and different cross sectional diameters. FIG. 14 establishes that the number of unit cells arrayed across the cross section does not impact the radial compression force but the cross sectional diameter has a significant impact on the radial compression force of the IVR. The designs compared in FIGS. 14 through 16 are described in FIG. 6, with the nomenclature of each including the Unit cell/# of arrayed unit cells/O.D./C.S./design feature ("b" for bands or "none" for no bands. For example, B/2/54/7.6/b is design A in FIG. 6, B/3/54/7.6/b is design B, B/4/54/7.6/b is design C, B/2/54/4/b is design H, etc.

FIG. 15 compares IVRs made using FPU 230 and the same unit cell and arrays with and without the added design feature of the banding on the inner and outer diameter. FIG. 15 establishes that while there is not a significant difference between the F10 of IVRs with different numbers of unit cells arrayed across the cross section, the added design feature of the banding has a significant impact on the radial compression force.

FIG. 16 compares IVRs of the same size and material and the same added design features with three different unit cell designs. The specific surface area (SSA) (surface area/volume) of the BB based IVR is equivalent to the SSA of the DD based IVR. The DD and EE unit cells are the same size but the DD, EE, and BB IVRs have different SSA. FIG. 16 establishes that the unit cell design and size impacts the radial compression force.

Example 6

Fluorescence Microscopy i. Effect of Light Intensity on Fluorophore Distribution To evaluate the effect of photon flux on drug loading within the IVR, IVRs were fabricated at three light intensities (3.45 mW/cm$^2$, 4.60 mW/cm$^2$, and 5.75 mW/cm$^2$) using the CLIP process. Each IVR was loaded with a fluorescent dye Rhodamine-B at 0.01 wt. %. Using fluorescence microscopy analysis, a cross-sectional view at two magnifications for IVRs fabricated at varying light intensities shows that the distribution of fluorophore appears homogenous throughout the cross-section of the part (FIGS. 8A through 8F).

Fluorescence imaging is shown in FIGS. 8A through 8F. Cross-sectional views are shown at two magnifications for prototype IVRs fabricated at varying light intensities of 5.75 mW/cm$^2$ (FIGS. 8A and 8B), 4.60 mW/cm$^2$, and (FIGS. 8C and 8D), and 3.45 mW/cm$^2$ (FIGS. 8E and 8F). Distribution of fluorophore (0.01 wt. % rhodamine-B) appears homogenous throughout the cross-section of each IVR fabricated with the CLIP process.

The ESEM analysis also shows that CLIP light intensity as a fabrication parameter does not affect the homogenous distribution of fluorophore in a CLIP fabricated IVR. This allows fabrication of IVRs with varying mechanical properties without altering the distribution of a drug molecule within the IVR.

ii. Effect of Unit Cell on Fluorophore Distribution

The effect of varying the unit cell properties on the distribution of a small molecule drug within the IVR fabricated using the CLIP process was also investigated. Using CAD files, IVRs with three different unit cells (AA, BB and CC) were fabricated. The IVRs contained 0.01 wt. % of rhodamine-B as a fluorescent dye. Using fluorescence analysis, a cross-sectional view at two magnifications for each of unit cells AA, BB and CC shows that the distribution of fluorophore appears homogenous throughout the cross-section of the IVR (FIGS. 9A through 9F).

FIGS. 9A through 9F are fluorescence images of cross-sectional views, at two magnifications, of each of unit cells AA (FIGS. 9A and 9B) BB (FIGS. 9C and 9D) and CC (FIGS. 9E and 9F). Distribution of fluorophore (0.01 wt. % rhodamine-B) appears homogenous throughout the cross-section of each IVR fabricated with the CLIP process.

This data demonstrates that input unit cell does not affect the homogenous distribution of a small molecule like the fluorophore rhodamine-B in a CLIP fabricated IVR. This is important in that it demonstrates that the formulation of a small molecule within the IVR having varying unit cells will be achieved with a homogenous distribution of the molecule drug within the IVR. This is particularly important in drug delivery, whereby a homogenous distribution of a drug molecule within a device is necessary to predict and maintain steady and reproducible release of the drug molecule from the device.

Example 7

Continuous Liquid Interface Production of Biocompatible Intravaginal Rings

Towards developing a biocompatible IVR, IVR prototypes with different unit cells were fabricated using a resin based on Poly(ethylene glycol) diacrylate ($M_n$=575), Poly(ethylene glycol) diacrylate ($M_n$=700), ethyl (2,4,6-trimethyl benzyol) phenylphosphinate, and 2-(3'-tert-butyl-2'-hydroxy-5'-methylphenyl)-5-chlorobenzotriazole (FIGS. 10A through 10O). PEG is an FDA registered biocompatible material that has been used in a number of pharmaceutical and biomedical drugs and devices. Using CAD files, IVRs with three different unit cells (unit cells AA in IVR 102, BB in IVR 104 and CC in IVR 106; FIGS. 10A, 10B and 100, respectively) were fabricated. The IVRs contained 0.01 wt. % of rhodamine-B as a fluorescent dye to investigate the effect of unit cell properties (shape and size) on the release of rhodamine-B from the IVRs in vitro.

Example 8

Fabrication of PEG CLIP IVR with Multiple Unit Cells within a Single IVR Unit

Another advantage of 3D printing is the ability to rapidly design and fabricate an IVR with multiple unit cells that vary in size and shape in a single unit. As disclosed herein, a CAD file of a single IVR containing three different unit cells was successfully developed. Using CLIP, a PEG-based IVR having three different unit cell dimensions in a single unit (FIGS. 11A and 11B) was successfully fabricated.

FIGS. 11A and 11B show intravaginal rings 108 containing three unit cells of varying size (3.0 mm, 2.5 mm and 2.0 mm) fabricated using CLIP with a PEG 700 diacrylate resin (FIG. 11A: CAD file design of multi unit cell IVR; FIG. 11B CLIP human size IVR containing 0.01% w/w rhodamine-B (55 mm O.D., 5 mm C.S.).

This rapidly fabricated IVR shows the ability to not only fabricate IVRs with varying unit cells and complex geometries, but also vary complex geometries within a single IVR matrix. This is an unprecedented feature unique to 3D printing that cannot be achieved with injection molding and hot-melt extrusion. Having immediate control over the number and area of complex geometries that can be included within a single IVR unit opens up a number of other possibilities to fine tune drug loading and release from the IVR.

Example 9

Design and Fabrication of Unsymmetrical IVRs

As illustrated in FIGS. 12A and 12B, the complexity of the IVR can be extended to design and fabricate IVRs with unsymmetrical shapes, for example an oval-shaped IVR with unit cell geometry like the one shown in FIGS. 12A and 12B. FIG. 12A is an illustration of a CAD file of an example oval-shaped IVR 120, with FIG. 12B an image of a prototype 3D printed IVR 120. IVR 120 can in some embodiments comprise an outer surface OS, inner surface IS and be made of any type of unit cells, including for example unit cells BB. In some aspects such an IVR can include convex portions 122 on inner surface IS, as shown in FIG. 12B. This shows the flexibility to not only design IVRs with complex geometries within the ring, but also IVRs with complex shape and shape design where the O.D. and C.S. of the ring designs do not have to be consistent across the entire ring.

Example 10

In Vitro Release Studies i. In Vitro Release of Rhodamine-B from IVRs Fabricated with a Range of Unit Cell Designs In this study the effect of unit cell dimensions on the release profile of small molecules from IVRs fabricated with the CLIP process were investigated. IVRs with three different unit cells containing 0.01 wt. % rhodamine-B were fabricated with the CLIP process at a photon flux of 5.75 mW/cm$^2$. The ability to control the specific surface area of the IVRs is unique to the 3D printing process, and in some embodiments other 3D printing methodologies, and allows the ability to tune and control the release of drug molecules from the IVR. By increasing the specific surface area, the area exposed to the release medium is increased resulting in enhanced dissolution and greater drug release. In vitro release studies of unit cell AA (surface area 10114 mm$^2$, N=3), unit cell BB (surface area 7688 mm$^2$, N=3), and unit cell CC (surface area 7404 mm$^2$, N=3) show that the release of rhodamine-B from BB was greater than the release from AA and CC. Unit cell BB IVR has the highest specific surface area and therefore exhibits a greater release of rhodamine-B as illustrated in FIG. 17.

FIG. 17 shows in vitro release of rhodamine-B from IVRs (N=3) over 33 days at 37° C. in 25 mM NaOAc buffer (pH 4.2). IVRs were fabricated with the CLIP process at varying unit cells, including AA IVR with 10114 mm$^2$ specific surface area, BB IVR with 7688 mm$^2$ specific surface area, and CC IVR with 7404 mm$^2$ specific surface area. Larger specific surface area and pore size within the unit cell results in greater release of rhodamine-B from the IVR.

Unit cell CC IVR exhibited a greater release of rhodamine-B compared to AA IVR despite the fact that CC specific surface area is slightly smaller than that of AA. Looking closely at the shape and dimensions of the unit cells in AA and CC, CC unit cell has greater pore dimensions compared to the unit cell in AA (FIG. 5). The greater pore size in CC allows faster diffusion of rhodamine-B from the IVR resulting in greater release as illustrated in FIG. 17. This demonstrates that the shape and dimensions of the unit cell can also influence the release of rhodamine-B from the IVR.

ii. In Vitro Release of β-Estradiol from IVRs Fabricated with High and Low Unit Cell Sizes: Effect of SSA and Fractional Volume on Release Kinetics of β-Estradiol.

Drug loaded IVRs were prepared and tested for release characteristics as follows. 929 mg of β-Estradiol was dissolved into 52 g of pre-mixed FPU 230 (Carbon) resin using a Thinky ARE310 mixer for 10 minutes at 2000 rpm. The drug loaded resin was placed into the M1 (Carbon) CLIP machine tray. The .stl file representing a single IVR based on the DD unit cell with 1 unit cell arrayed across the 7.6 mm cross section and an outer diameter of 54 mm was loaded into the M1 software for printing. The IVR was printed in approximately 8 minutes. The printed IVR was cleaned using the standard method provided for M1 printing of IVRs. Four replicate D/1 54/7.6 samples were printed and cleaned as above. A second batch of drug loaded FPU 230 was prepared in an analogous procedure using 498 mg of β-Estradiol and 52 g of pre-mixed FPU 230. The .stl file representing a single IVR based on the D unit cell with 2 units arrayed across the 7.6 mm cross section and an outer diameter of 54 mm was loaded into the M1 software for printing. Four replicate D/2 54/7.6 samples were printed and cleaned as above. The 8 rings were transferred to a 120° C. forced air oven for 4 hours and removed and cooled on a tray.

Release testing in simulated vaginal fluid (SVF) was conducted using the procedure for release studies of IVRs in SVF provided. An initial burst release of approximately 20% of the cargo over the first 2 days was observed for both sets of rings. A steady release rate is observed from days 2 to 58 with the D/2 ring releasing at a higher level and a higher rate than the D/1 ring. The rate of release for each ring was measured as the slope of the line between 2 and 58 days. D/2 with a fractional volume of 0.443 and measured specific surface area (SSA) (surface area/volume) of 4.5 was found to release at a rate of 240 μg/day and D/1 with a fractional volume of 0.318 and measured SSA of 2.9 was found to release at a rate of 189 μg/day. Results are provided in Table 3 and graphs are provided in FIG. 18.

TABLE 3

In vitro release of β-Estradiol for D series IVRs tested in SVF.

| Ring | Drug Loading (mg/ring) | Fractional Volume | Measured SSA (mm$^{-1}$) | % Released Initially (days 0-2) | Release Rate (μg/day) (days 2-58) |
|---|---|---|---|---|---|
| D/1 | 24 | 0.318 | 2.9 | 24 | 189 |
| D/2 | 24 | 0.443 | 4.5 | 26 | 240 | iii. In Vitro Release of β-Estradiol from IVRs Fabricated with a Range of Unit Cell Sizes: Effect of Unit Cell Dimensions on Release Kinetics of β-Estradiol.

A series of IVRs were printed using the standard method for printing with the M1 3D CLIP printer. The resin was prepared with approximately 3-weight % 6-Estradiol in premixed FPU 230 in a Thinky ARE310 mixer for 10 minutes at 2000 rpm. The series of IVRs were based on a BB unit cell design with a 54 mm outer diameter and a 7.6 mm cross section and included banding of 0.5 mm on the inner and outer diameters of the IVRs. Three designs are represented by the unit cell B arrayed 2, 3, and 4 wide across the IVR cross-section (Design A, Design B, and Design C, respectively, in FIG. 19, details of which can be found in FIG. 6). The fourth design includes all three unit cell sizes distributed in two segments each around the IVR and connected by solid portion linkers (Design D in FIG. 19). Four IVR replicates of each of four designs were fabricated and tested for drug release in SVF using the method described. Table 3 provides the theoretical and measured characteristics of the IVRs and their steady release rates. FIG. 19 provides the cumulative % release of β-Estradiol over time. All of the IVRs released approximately 20% of their cargo in the first 5 days before settling to a steady rate of release measured as the slope of the cumulative release per day from day 4 to the end of test. The release rate trend is consistent with the fractional volume and theoretical SSA for the B/2, B/3, and BA rings. The Trimodal ring would be expected to be most similar to the B/2 ring in release rate based on the theoretical SSA or most similar to the BA ring based on the fractional volume but it is seen to fall in between these values. Because there is additional design complexity in the Trimodal ring, based on the distribution of unit cell sizes and the solid connectors between regions, the Trimodal IVR is not directly comparable to the other, more similar, BB unit cell IVR designs. Table 4 establishes that the complexity of design affects the rate of release in a predictable manner with constant design features.

TABLE 4

Volume data for B series (Unit cell BB) rings tested in SVF with β-Estradiol loaded IVRs.

| Ring | Fractional Volume | Theoretical SSA (mm–$^1$) | Loading (mg/Ring) | Steady release rate (μg/day) | Days to Maximum Release (% Released) |
|---|---|---|---|---|---|
| B/2 banded | 0.475 | 6.9 | 108 | 544 | 115 (80) |
| B/3 banded | 0.577 | 9.2 | 107 | 741 | 105 (100) |
| B/4 banded | 0.638 | 11.5 | 142 | 926 | 112 (100) |
| B/Trimodal banded | 0.668 | 6.7 | 141 | 707 | 115 (77) | iv. In Vitro Release of β-Estradiol from IVRs Fabricated with 3 Different Unit Cells: Effect of Unit Cell Geometry (i.e. Unit Cell Design and Microscopic Architecture) on the Release Kinetics of β-Estradiol Three weight % β-Estradiol was dissolved in premixed FPU 230 resin using a Thinky ARE310 mixer for 10 minutes at 2000 rpm. Geometrically complex IVR designs based on the D and E unit cells arrayed 2.6 times across the width of a 7.6 mm cross section 54 mm outer diameter IVR including a 0.5 mm band on the inner and outer diameters of the IVR were fabricated per the method of printing IVRs using the M1 3D CLIP printer with the drug loaded FPU 230 resin. Four replicate rings of each IVR design were prepared and tested for drug release in SVF per the method for SVF release of IVRs provided. The characteristics and release rates of the rings are compared to a unit cell B IVR design in Table 5. The cumulative percent release of these rings (unit cell DD (UCD), unit cell EE (UCE) and unit cell BB (UCB) is provided in FIG. 20. Release rate was measured as the slope of the cumulative release rate from day 4 to the end of the test. Table 5 establishes that the average release rate is controlled by the fractional volume produced through the unit cell design and drug loading level.

TABLE 5

Volume data for B/3, D/2.6, and E/2.6 IVRs tested in SVF with β-Estradiol loaded IVRs (note, B/3 tested in Study iii).

| Ring | Fractional Volume | Theoretical SSA (mm$^{-1}$) | Loading (mg/Ring) | Release rate (μg/day) | Days to Max Release (%) |
|---|---|---|---|---|---|
| B/3 banded | 0.577 | 9.2 | 107 | 741 | 105(100) |
| D/2.6 banded | 0.695 | 9.4 | 171 | 787 | 102(68) |
| E/2.6 banded | 0.444 | 13.1 | 82 | 468 | 92(100) | v. In Vitro Release of β-Estradiol from Geometrically Complex IVRs Fabricated with 3 Different Drug Concentrations: Effect of Drug Loading on Release Kinetics IVR designs based on the B unit cell arrayed 2 times (Design A from FIG. 6) and 4 times (Design C from FIG. 6) across the width of a 7.6 mm cross section of a 54 mm outer diameter ring with a 0.5 mm band on the inner and outer diameters of the rings were prepared with β-Estradiol loaded at three different concentrations at approximately one log-increment in % weight of β-Estradiol (i.e. 10% (high), 1% (medium), and 0.1% (low) w/w). Four replicate rings of each design and loading were fabricated using the M1 printing procedure provided and tested for release per the release testing method provided. Table 6 provides the characteristics and release results of the IVRs of different designs and drug loadings. The release kinetics shows a biphasic kinetics with a greater release rate in the first two to four days followed by more steady release rate over time for all samples and corresponded to the loading level such that for the low and medium loaded samples the burst release was on the order of 10% while for the high loading samples the burst release was on the order of 1%. This indicates that a concentration dependent diffusion limit is reached between the medium and high loading level. The amount released per day over the long term of the study increased with loading level and the % released per day shows a decreasing trend from about 1.3 to 0.5% from the low to the high loading. The cumulative released amount and the cumulative % released for this set of rings is provided in the graphs in FIGS. 21 and 22. These graphs show that the overall percentage released decreases with increasing loading level. At all loading levels the B4 design (Design C from FIG. 6) with higher fractional volume and theoretical SSA releases more drug faster than the B2 design (Design A from FIG. 6). These results establish that both IVR design complexity and drug loading level are used to control drug release over time.

TABLE 6

Volume data for B/2 (Design A from FIG. 6) and B/4 (Design C from FIG. 6) IVRs tested in SVF in Study iv and study ii at low, medium, and high loading levels of β-Estradiol.

| Ring | Fractional Volume | Drug loading (mg/ring) | Release rate day 1 (μg/day) [%] | Release rate 4-End (μg/day) [%/day] | Days to Max Release (%) |
|---|---|---|---|---|---|
| B/2 banded low | 0.508 | 0.58 | 67 [11.6] | 8 [1.3] | 57 (100) |
| B/2 banded med | 0.485 | 7.8 | 931 [11.9] | 64 [0.8] | 71 (82) |
| B/2 banded high | 0.475 | 107.8 | 1319 [1.2] | 544 [0.5] | 115 (80) |

TABLE 6-continued

Volume data for B/2 (Design A from FIG. 6) and B/4 (Design C from FIG. 6) IVRs tested in SVF in Study iv and study ii at low, medium, and high loading levels of β-Estradiol.

| Ring | Fractional Volume | Drug loading (mg/ring) | Release rate day 1 (μg/day) [%] | Release rate 4-End (μg/day) [%/day] | Days to Max Release (%) |
|---|---|---|---|---|---|
| B/4 banded low | 0.637 | 1.22 | 111 [9.1] | 15 [1.2] | 64 (100) |
| B/4 banded med | 0.624 | 11.8 | 1202 [10.2] | 122 [1.0] | 71 (100) |
| B/4 banded high | 0.638 | 141.9 | 1387 [1.0] | 926 [0.6] | 112 (100) | vi. In Vitro Release of β-Estradiol from IVRs Fabricated with Different Macroscopic Architectures: Effect of IVR Dimensions (CS) on Release Kinetics.

β-Estradiol was dissolved into pre-mixed FPU 230 (Carbon) resin using a Thinky ARE310 mixer for 10 minutes at 2000 rpm at a range of concentrations and used to fabricate IVRs per the method for M1 printing of IVRs provided. Four replicates of each design and loading were fabricated and tested for release per the SVF release procedure for IVRs provided. Table 6 provides the characteristics of the geometrically complex IVRs fabricated and compared. IVR designs incorporating the B unit cell into a smaller and larger cross section are compared. The 4 mm and 7.6 mm cross section designs compared have approximately equivalent theoretical SSA of about 11.4 (Table 7). The 7.6 mm cross section IVR design is banded on the inner and outer diameters with a 0.5 mm band and the 4 mm cross section design IVR is unbanded. These data show that the 4 mm cross section unbanded IVRs release their cargo faster than the 7.6 mm banded IVRs and establish that design factors, including IVR macroscopic dimensions, and drug loading level impact the release characteristics of the IVRss (FIGS. 23A and 23B).

TABLE 7

Effect of IVR dimensions (CS) on release kinetics

| Loading (wt %) | Loading (mg/Ring) | Design (#UC/CS) | OD/CS (mm) | Release rate (μg/day) [%/day] 4-end days | Days to Max Release (%) |
|---|---|---|---|---|---|
| 4.8 | 42.7 (high) | B/2.02 | 54/4 | 706 [1.7] | 32 (100) |
| 0.84 | 7.3 (med) | B/2.02 | 54/4 | 85 [1.2] | 50 (100) |
| 0.28 | 11.8 (med) | B/4 banded | 54/7.6 | 122 [1.0] | 71 (100) |
| 0.028 | 1.22 (low) | B/4 banded | 54/7.6 | 15 [1.2] | 64 (100) |
| 3.2 | 141.9 (high) | B/4 banded | 54/7.6 | 926 [0.6] | 112 (100) | vii. In Vitro Release of Progesterone from IVRs

A resin was prepared to contain the following: poly (ethylene glycol) dimethyacrylate (Mn=750, PEG DMa), isobornyl methacrylate. These efforts were focused on the synthesis and characterization of perfluoroether based polymer liquid electrolytes. Polymer synthesis, chemical modification, and characterization were carried out at the University of North Carolina. Liquid perfluoroether electrolyte samples were provided to University of California, Berkeley and Stonybrook University for electrochemical analysis and evaluation. A basis of this work to identify the potential for the use of PFPE diol and dimethyl carbonate functionalized oligomers was previously reported [31]. The following was used to synthesize and characterize liquid perfluoroether (PPFE) electrolytes with a variety of chemical modifications. (IBOMa), ethyl (2,4,6-trimethyl benzyol) phenylphosphinate (EtmPP), and 2-(3'-tert-butyl-2'-hydroxy-5'-methylphenyl)-5-chlorobenzotriazole (BLS 1326) were used. The formulation was comprised of PEG DMa (48.4 wt. %), IBOMa (48.4 wt. %), EtmPP (3 wt. %), and BLS 1326 (0.2 wt. %). Resin components were mixed in a Thinky ARE310 mixer for 5 minutes at 2000 rpm.

The PEG-based resin was loaded with Progesterone in a range of concentrations by mixing in the Thinky ARE310 mixer for 5 minutes at 2000 rpm. Progesterone was loaded at approximately 7 (high), 0.7 (medium), and 0.07 (low) weight percent into the resin. A series of IVRs were fabricated on the M1 using the B unit cell design with a 54 mm outer diameter, 7.6 mm cross-section and 0.5 mm band thickness. IVRs containing 2 and 3 unit cells across the cross-section were fabricated at the high loading and IVRs containing 2 and 4 unit cells across the cross-section were fabricated at the medium and low loadings. IVRs were removed from the build platform and patted dry using a lint free towel to remove uncured surface resin. Compressed air was applied to each side of the IVRs for approximately 30 s on each side to remove residual resin. IVRs were then post-cured in a 365 nm LED oven for 2 minutes at roughly 20 mW/cm$^2$.

The IVRs were subjected to a release study in simulated vaginal fluid per the previously presented procedure. The cumulative release in micrograms/ring and the cumulative % release are provided in FIGS. 24A and 24B, respectively, showing release profiles that differ as a function of fractional volume (IVR) and loading (drug). The release results for the progesterone loaded IVRs in Table 8 can be compared to the same IVR designs made using FPU 230 and loaded with β-Estradiol in the previous example. The progesterone loaded PEG IVRs of similar loading and volume fractions release progesterone at a faster rate than the β-Estradiol is released from the FPU 230 IVRs. These results establish that the release rate is a function of the IVR material and the drug combination as well as the design and loading of the IVRs.

TABLE 8

Progesterone release results

| IVR | Average drug Loading (mg/ring) | Volume Fraction | Release Rate (µg/day) (day 2-end) | Days to End (% Released at End) |
|---|---|---|---|---|
| B/2 Banded | 248 | 0.475 | 1806 | 47 (40) |
| B/3 Banded | 289 | 0.543 | 1826 | 47 (35) |
| B/2 Banded | 19 | 0.374 | 216 | 47 (92) |
| B/4 Banded | 24 | 0.510 | 234 | 47 (76) |
| B/2 Banded | 1.9 | 0.395 | 27 | 43 (100) |
| B/4 Banded | 1.8 | 0.470 | 31 | 33 (100) |

REFERENCES

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

[1] http://www.who.int/features/factfiles/hiv/en/, WHO—10 Facts on HIV/AIDS, (2015).

[2] R. M. Grant, J. R. Lama, P. L. Anderson, V. McMahan, A. Y. Liu, L. Vargas, P. Goicochea, M. Casapia, J. V. Guanira-Carranza, M. E. Ramirez-Cardich, O. Montoya-Herrera, T. Fernandez, V. G. Veloso, S. P. Buchbinder, S. Chariyalertsak, M. Schechter, L. G. Bekker, K. H. Mayer, E. G. Kailas, K. R. Amico, K. Mulligan, L. R. Bushman, R. J. Hance, C. Ganoza, P. Defechereux, B. Postle, F. Wang, J. J. McConnell, J. H. Zheng, J. Lee, J. F. Rooney, H. S. Jaffe, A. I. Martinez, D. N. Burns, D. V. Glidden, Preexposure chemoprophylaxis for HIV prevention in men who have sex with men, N Engl J Med, 363 (2010) 2587-2599.

[3] P. L. Anderson, D. V. Glidden, A. Liu, S. Buchbinder, J. R. Lama, J. V. Guanira, V. McMahan, L. R. Bushman, M. Casapia, O. Montoya-Herrera, V. G. Veloso, K. H. Mayer, S. Chariyalertsak, M. Schechter, L. G. Bekker, E. G. Kailas, R. M. Grant, Emtricitabine-tenofovir concentrations and pre-exposure prophylaxis efficacy in men who have sex with men, Sci Transl Med, 4 (2012) 151ra125.

[4] J. M. Baeten, D. Donnell, P. Ndase, N. R. Mugo, J. D. Campbell, J. Wangisi, J. W. Tappero, E. A. Bukusi, C. R. Cohen, E. Katabira, A. Ronald, E. Tumwesigye, E. Were, K. H. Fife, J. Kiarie, C. Farquhar, G. John-Stewart, A. Kakia, J. Odoyo, A. Mucunguzi, E. Nakku-Joloba, R. Twesigye, K. Ngure, C. Apaka, H. Tamooh, F. Gabona, A. Mujugira, D. Panteleeff, K. K. Thomas, L. Kidoguchi, M. Krows, J. Revall, M. Morrison, H. Haugen, M. Emmanuel-Ogier, L. Ondrejcek, R. W. Coombs, L. Frenkel, C. Hendrix, N. N. Bumpus, D. Bangsberg, J. E. Haberer, W. S. Stevens, J. R. Lingappa, C. Celum, Antiretroviral prophylaxis for HIV prevention in heterosexual men and women, N Engl J Med, 367 (2012) 399-410.

[5] D. Donnell, J. M. Baeten, N. N. Bumpus, J. Brantley, D. R. Bangsberg, J. E. Haberer, A. Mujugira, N. Mugo, P. Ndase, C. Hendrix, C. Celum, HIV protective efficacy and correlates of tenofovir blood concentrations in a clinical trial of PrEP for HIV prevention, J Acquir Immune Defic Syndr, 66 (2014) 340-348.

[6] L. Van Damme, A. Corneli, K. Ahmed, K. Agot, J. Lombaard, S. Kapiga, M. Malahleha, F. Owino, R. Manongi, J. Onyango, L. Temu, M. C. Monedi, P. Mak'Oketch, M. Makanda, I. Reblin, S. E. Makatu, L. Saylor, H. Kiernan, S. Kirkendale, C. Wong, R. Grant, A. Kashuba, K. Nanda, J. Mandala, K. Fransen, J. Deese, T. Crucitti, T. D. Mastro, D. Taylor, Preexposure prophylaxis for HIV infection among African women, N Engl J Med, 367 (2012) 411-422.

[7] J. G. Garcia-Lerma, W. Heneine, Animal models of antiretroviral prophylaxis for HIV prevention, Curr Opin HIV AIDS, Early online publication (2012).

[8] C. W. Hendrix, The clinical pharmacology of antiretrovirals for HIV prevention, Curr Opin HIV AIDS, Early online publication (2012).

[9] J. A. Higgins, S. Hoffman, S. L. Dworkin, Rethinking Gender, Heterosexual Men, and Women's Vulnerability to HIV/AIDS, Am J Public Health, 100 (2010) 435-445.

[10] P. F. Kiser, T. J. Johnson, J. T. Clark, State of the Art in Intravaginal Ring Technology for Topical Prophylaxis of HIV Infection, Aids Rev, 14 (2012) 62-77.

[11] S. Koetsawang, G. Ji, U. Krishna, A. Cuadros, G. I. Dhall, R. Wyss, J. Rodriquez la Puenta, A. T. Andrade, T. Khan, E. S. Konova, et al., Microdose intravaginal levonorgestrel contraception: a multicentre clinical trial. IV. Bleeding patterns. World Health Organization. Task Force on Long-Acting Systemic Agents for Fertility Regulation, Contraception, 41 (1990) 151-167.

[12] D. R. Mishell, Jr., M. E. Lumkin, Contraceptive effect of varying dosages of progestogen in silastic vaginal rings, Fertil Steril, 21 (1970) 99-103.

[13] E. Weisberg, I. S. Fraser, J. Baker, D. Archer, B. M. Landgren, S. Killick, P. Soutter, T. Krause, C. d'Arcangues, A randomized comparison of the effects on vaginal and cervical epithelium of a placebo vaginal ring with non-use of a ring, Contraception, 62 (2000) 83-89.

[14] WHO-UNAIDS, http://www.who.int/hiv/pub/progress_report2011/en/index.html, S. Geneva, (2013).

[15] P. H. Kilmarx, Global epidemiology of HIV, Curr Opin Hiv Aids, 4 (2009) 240-246.

[16] Q. A. Karim, S. S. A. Karim, J. A. Frohlich, A. C. Grobler, C. Baxter, L. E. Mansoor, A. B. M. Kharsany, S. Sibeko, K. P. Mlisana, Z. Omar, T. N. Gengiah, S. Maarschalk, N. Arulappan, M. Mlotshwa, L. Morris, D. Taylor, C. T. Grp, Effectiveness and Safety of Tenofovir Gel, an Antiretroviral Microbicide, for the Prevention of HIV Infection in Women, Science, 329 (2010) 1168-1174.

[17] clinicaltrials.gov, Intravaginal Rings, (2015).

[18] I. Lete, J. L. Doval, E. Perez-Campos, R. Lertxundi, M. Correa, E. de la Viuda, M. A. Gomez, J. V. Gonzalez, M. T. Martinez, N. Mendoza, J. Robledo, Self-described impact of noncompliance among users of a combined hormonal contraceptive method, Contraception, 77 (2008) 276-282.

[19] E. Hardy, E. M. Hebling, M. H. Sousa, A. F. Almeida, E. Amaral, Delivery of microbicides to the vagina: difficulties reported with the use of three devices, adherence to use and preferences, Contraception, 76 (2007) 126-131.

[20] M. D. Creinin, L. A. Meyn, L. Borgatta, K. Barnhart, J. Jensen, A. E. Burke, C. Westhoff, M. Gilliam, C. Dutton, S. A. Ballagh, Multicenter comparison of the contraceptive ring and patch—A randomized controlled trial, Obstet Gynecol, 111 (2008) 267-277.

[21] A. Szarewski, High acceptability and satisfaction with NuvaRing use, Eur J Contracep Repr, 7 (2002) 31-36.

[22] C. Brucker, U. Karck, E. Merkle, Cycle control, tolerability, efficacy and acceptability of the vaginal contraceptive ring, NuvaRing (R): Results of clinical experience in Germany, Eur J Contracep Repr, 13 (2008) 31-38.

[23] G. Dezarnaulds, I. S. Fraser, Vaginal ring delivery of hormone replacement therapy—a review, Expert Opin Pharmaco, 4 (2003) 201-212.

[24] B. A. Chen, L. Panther, M. A. Marzinke, C. W. Hendrix, C. J. Hoesley, A. van der Straten, M. J. Husnik, L. Soto-Torres, A. Nel, S. Johnson, N. Richardson-Harman, L. K. Rabe, C.S. Dezzutti, Phase 1 Safety, Pharmacokinetics, and Pharmacodynamics of Dapivirine and Maraviroc Vaginal Rings: A Double-Blind Randomized Trial, J Acquir Immune Defic Syndr, 70 (2015) 242-249.

[25] J. R. Tumbleston, D. Shirvanyants, N. Ermoshkin, R. Janusziewicz, A. R. Johnson, D. Kelly, K. Chen, R. Pinschmidt, J. P. Rolland, A. Ermoshkin, E. T. Samulski, J. M. DeSimone, Continuous liquid interface production of 3D objects, Science, 347 (2015) 1349-1352.

[26] D. H. Owen, D. F. Katz, A vaginal fluid simulant, Contraception, 59 (1999) 91-95.

[27] S. R. Ugaonkar, A. Wesenberg, J. Wilk, S. Seidor, O. Mizenina, L. Kizima, A. Rodriguez, S. Zhang, K. Levendosky, J. Kenney, M. Aravantinou, N. Derby, B. Grasperge, A. Gettie, J. Blanchard, N. Kumar, K. Roberts, M. Robbiani, J. A. Fernandez-Romero, T. M. Zydowsky, A novel intravaginal ring to prevent HIV-1, HSV-2, HPV, and unintended pregnancy, J Control Release, 213 (2015) 57-68.

[28] N. Alharbi, R. Osman, D. Wismeijer, Effects of build direction on the mechanical properties of 3D-printed complete coverage interim dental restorations, J Prosthet Dent, (2016).

[29] J. T. Clark, T. J. Johnson, M. R. Clark, J. S. Nebeker, J. Fabian, A. L. Tuitupou, S. Ponnapalli, E. M. Smith, D. R. Friend, P. F. Kiser, Quantitative evaluation of a hydrophilic matrix intravaginal ring for the sustained delivery of tenofovir, J Control Release, 163 (2012) 240-248.

[30] K. T. Barnhart, K. Timbers, E. S. Pretorius, K. Lin, A. Shaunik, In vivo assessment of NuvaRing placement, Contraception, 72 (2005) 196-199.

[31] J. L. T. Dominica H. C. Wong, Yanbao Fu, Didier Devaux, Ashish A. Pandya, Vincent S. Battaglia, Nitash P. Balsara, and Joseph M. DeSimone, Nonflammable perfluoropolyether-based electrolytes for lithium batteries, PNAS Early Edition, (2013) 1-5.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of fabricating a 3D printed intravaginal ring (IVR), comprising:
   providing a template for the IVR, the template comprising:
   a three dimensional ring structure comprising a body forming an inner diameter and an outer diameter;
   a plurality of unit cells, each of the unit cells comprising a macroscopic architecture and/or microscopic architecture, wherein each of the unit cells forms a geometric shape, wherein the plurality of unit cells together form the body of the ring structure, wherein the IVR comprises one or more types of unit cells, wherein each type of unit cell varies in size, shape, configuration, surface area and/or three dimensional geometry; and
   a void volume that is regularly or irregularly distributed continuously or in discrete volumes amongst the plurality of unit cells, wherein the void volume is greater than or equal to about 10;
   providing a material from which the IVR is to be fabricated;
   providing a 3D printing system; and
   producing the IVR from the material using the 3D printing system based on the template.

2. The method of claim 1, further comprising providing an active compound, wherein the active compound is incorporated into the IVR during or after 3D printing.

3. The method of claim 1, further comprising providing an active compound, wherein the active compound is captured inside one or more nanoparticles incorporated into the IVR.

4. The method of claim 1, further comprising providing an active compound, wherein the active compound is incorporated into the IVR after 3D printing by coating, absorption, infusion, or adsorption of the active compound onto the IVR.

5. The method of claim 1, further comprising providing a gel compound, wherein the gel compound is incorporated into the IVR after 3D printing by filling the void volume of the IVR.

6. The method of claim 2, wherein the active compound comprises a therapeutic compound selected from a group consisting of an antiviral, antiretroviral, microbicide, contraceptive, antibiotic, biologics, hormone, pre-exposure prophylaxis, small molecule drug, macromolecule drug, biopharmaceutical, chemotherapeutic, other pharmaceutical compound, and combinations thereof.

7. The method of claim 2, wherein the plurality of unit cells are configured to control a loading capacity of the active compound within or on the IVR, a diffusion of the active compound from the IVR, a surface area of the IVR, and/or mechanical properties of the IVR.

8. The method of claim 1, wherein the 3D printing system comprises a Continuous Liquid Interface Production (CLIP) system.

9. The method of claim 1, wherein a shape, size, and/or surface area within the IVR is produced by the 3D printing.

10. The method of claim 1, wherein physical and mechanical properties of the IVR are controlled by light intensity, print time, or print orientation during or after the 3D printing, the material used during the 3D printing, and/or a degree of cross-linking during or after the 3D printing.

11. The method of claim 1, further comprising providing a computer readable medium having stored thereon executable instructions that when executed by a processor of a computer control the computer to perform the method.

12. The method of claim 11, wherein the computer readable medium having stored thereon the executable instructions that when executed by the processor of the computer control the computer to generate a virtual three dimensional template of the IVR.

13. The method of claim 11, wherein the computer readable medium having stored thereon the executable instructions that when executed by the processor of the computer control the computer to control the 3D printing system in communication with the computer, whereby the 3D printing system prints the IVR.

14. The method of claim 1, wherein the IVR template can comprise a standard tessellation language (STL) file, the IVR template comprises an IVR with the inner diameter of about 45 mm to about 65 mm and cross-sectional diameter of about 5 mm to about 15 mm and the IVR template comprises a unit cell or cells selected and arrayed within the IVR template to generate a geometrically complex part.

15. The method of claim 14, wherein the IVR template comprise the STL file, the IVR template comprises an IVR with a patient-specific inner diameter and cross-sectional diameter, a patient is selected from human, non-human primate, mouse or other mammal and the IVR template comprises a unit cell selected and arrayed within the template to generate a geometrically complex part.

16. The method of claim 1, wherein the IVR template can be iteratively used to generate scaffold IVRs comprised of different unit cells.

17. The method of claim 1, wherein the plurality of unit cells can range from about 0.1 mm to about 15 mm in three dimensions of X, Y and Z.

18. The method of claim 1, wherein the macroscopic architecture and/or microscopic architecture of the unit cells is configured to control a loading capacity of the active compound within or on the IVR, a diffusion rate of the active compound from the IVR, a surface area of the IVR, a fractional volume of the IVR, and/or a mechanical property of the IVR.

* * * * *